(12) United States Patent
Ma et al.

(10) Patent No.: US 11,197,912 B2
(45) Date of Patent: Dec. 14, 2021

(54) PREVENTION AND TREATMENT OF VIRAL INFECTION AND VIRAL INFECTION-INDUCED ORGAN FAILURE

(71) Applicant: TRIM-edicine, Inc., Columbus, OH (US)

(72) Inventors: Jianjie Ma, Powell, OH (US); Jacob S. Yount, Columbus, OH (US); Matthew A. Sermersheim, Nashville, TN (US); Adam D. Kenney, Columbus, OH (US); Xinyu Zhou, Hilliard, OH (US); Bryan A. Whitson, Westerville, OH (US); Nahush A. Mokadam, Upper Arlington, OH (US); Tao Tan, Columbus, OH (US); Chuanxi Cai, Powell, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 17/184,781

(22) Filed: Feb. 25, 2021

(65) Prior Publication Data

US 2021/0315968 A1  Oct. 14, 2021

Related U.S. Application Data

(63) Continuation-in-part of application No. PCT/US2020/028112, filed on Apr. 14, 2020.

(51) Int. Cl.
  *A61K 38/17* (2006.01)
  *A61K 45/06* (2006.01)

(52) U.S. Cl.
  CPC .......... *A61K 38/1709* (2013.01); *A61K 45/06* (2013.01)

(58) Field of Classification Search
  None
  See application file for complete search history.

(56) References Cited

U.S. PATENT DOCUMENTS

| | | |
|---|---|---|
| 7,981,866 B2 | 7/2011 | Ma |
| 8,420,338 B2 | 4/2013 | Weisleder |
| 8,603,992 B2 | 12/2013 | Ma |
| 8,603,993 B2 | 12/2013 | Ma |
| 9,139,630 B2 | 9/2015 | Ma |
| 9,458,465 B2 | 10/2016 | Weisleder |
| 9,494,602 B2 | 11/2016 | Weisleder |
| 9,505,821 B2 | 11/2016 | Ma |
| 2011/0202033 A1 | 8/2011 | Weisleder |
| 2011/0287015 A1 | 11/2011 | Ma |
| 2011/0287704 A1 | 11/2011 | Ma |
| 2012/0213737 A1 | 8/2012 | Zhu |
| 2013/0123340 A1 | 5/2013 | Ma |
| 2014/0024594 A1 | 1/2014 | Weisleder |
| 2015/0110778 A1 | 4/2015 | Ma |

FOREIGN PATENT DOCUMENTS

| | | |
|---|---|---|
| WO | 2008054561 A2 | 5/2008 |
| WO | 2008060776 A2 | 5/2008 |
| WO | 2009073808 A2 | 6/2009 |
| WO | 2010009312 A2 | 1/2010 |
| WO | 2010141810 A2 | 12/2010 |
| WO | 2011142744 A2 | 11/2011 |
| WO | 2012061793 A2 | 5/2012 |
| WO | 2012134478 A2 | 10/2012 |
| WO | 2012135868 A2 | 10/2012 |
| WO | 2013036610 A2 | 3/2013 |
| WO | 2016109638 A1 | 7/2016 |

OTHER PUBLICATIONS

Anonymous "Information for Clinicians on Investigational Therapeutics for Patients with COVID-19" https://www.cdc.gov/coronavirus/2019-ncov/hcp/therapeutic-options.html (Year: 2020).*
Bartoli et al. "COVID-19 treatment options: a difficult journey between failed attempts and experimental drugs" Internal and Emergency Medicine 16:281-308. (Year: 2021).*
Calwell E "Stopping lethal lung damage from the flu with a natural human protein" Ohio State News, https://news.osu.edu/stopping-lethal-lung-damage-from-the-flu-with-a-natural-human-protein/ (Year: 2020).*
Li et al. "MG53, A Tissue Repair Protein with Broad Applciations in Regenerative Medicine" Cells 10:122. (Year: 2021).*
Saraste et al. ("Coronary flow reserve and heart failure in experimental coxsackievirus myocarditis. A transthoracic doppler echocardiography study" in Amer. J. Physiol. Heart Circ. Physio. (2006), 291(2), 871-875).
Lee et al. ("A serine elastase inhibitor reduces inflammation and fibrosis and preserves cardiac function after experimentally-induced murine myocarditis" in Nat. Med. (1998), 4(12), 1383-1391).
Guo et al. ("Potential role of MG53 in the regulation of transforming-growth-factor-βi-induced atrial fibrosis and vulnerability to atrial fibrillation" in Exp. Cell Res. (2018), 362(2), 436-443; abstract).
Chen et al. ("TRIM72 contributes to cardiac fibrosis via regulating STAT3/Notch-1 signaling" in J. Cell. Physiol. (2019), 234(10), 17749-17756; abstract).
Liu et al. ("Upregulation of MG53 induces diabetic cardiomyopathy through transcriptional activation of peroxisome proliferation-activated receptor alpha" in Circ. (2015), 131(9), 795-804).
Hu et al. ("MG53 and disordered metabolism in striated muscle" in Biochim Biophys. Acta (2018), 1864(5), part B, 1984-1990; abstract).

\* cited by examiner

*Primary Examiner* — Sudhakar Katakam
*Assistant Examiner* — Zachary J Miknis
(74) *Attorney, Agent, or Firm* — Innovar, L.L.C.; Rick Matos

(57) ABSTRACT

Compositions for and methods of preventing, reversing or treating viral infection-induced organ failure provided. The compositions are also suitable for treating and/or preventing COVID-19 and influenza. The compositions and methods employ MG53, which can be in the form of recombinant human MG53. The MG53 may also be administered as a composition that expresses and releases MG53 after in vivo administration of said composition to a subject.

9 Claims, 15 Drawing Sheets

Specification includes a Sequence Listing.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: DNA 5' to 3' for shRNA

<400> SEQUENCE: 1
```

```
gactgacatg tcaagctgta c                                              21

<210> SEQ ID NO 2
<211> LENGTH: 29
<212> TYPE: DNA
<213> ORGANISM: Artificial Sequence
<220> FEATURE:
<223> OTHER INFORMATION: DNA 5' to 3' for shRNA

<400> SEQUENCE: 2
gaagagtgtg gctgtgctgg agcatcagc                                      29
```

PREVENTION AND TREATMENT OF VIRAL INFECTION AND VIRAL INFECTION-INDUCED ORGAN FAILURE

CROSS-REFERENCE TO EARLIER FILED APPLICATION

This application claims the benefit of and is a continuation-in-part of PCT/US20/28112 filed Apr. 14, 2020, the entire disclosure of which is hereby incorporated by reference.

STATEMENT REGARDING FEDERALLY SPONSORED RESEARCH

This invention was made with government support under grant/contract numbers R01 HL138570, R21 AI142256, R01 DK106394, T32 GM068412, R01 AR061385, R01 AR070752, and R01 AI130110 awarded by the National Institutes of Health; and grant/contract number W81XWH-18-1-0787 awarded by the U.S. Army Medical Research Acquisition Activity. The government has certain rights in the invention.

INCORPORATION BY REFERENCE

In compliance with 37 CFR 1.52(e)(5), the instant application contains Sequence Listings which have been submitted in electronic format via EFS and which are hereby incorporated by reference. The sequence information contained in electronic file named TRIM43PCT SEQ ST25.txt, size 1 KB, created on Apr. 14, 2020, using Patent-in 3.5.1, and Checker 4.4.6 is hereby incorporated by reference in its entirety.

FIELD OF THE INVENTION

The present invention concerns compositions for and methods of preventing, reversing, and/or treating viral infection-induced organ failure. A composition comprising (or expressing) a therapeutically effective amount of MG53 is administered to a subject suffering from a viral infection that induces organ failure, thereby preventing, reversing and/or treating organ failure. The invention also provides a method of decreasing the mortality rate in a population of subjects suffering from a viral infection that induces organ failure.

BACKGROUND OF THE INVENTION

The etiology of Organ failure (OF; also referred to as multiple organ dysfunction syndrome (MODS), multiple organ failure (MOF), total organ failure (TOF), multisystem organ failure (MSOF)) has not been fully characterized; however, uncontrolled inflammatory response, uncontrolled immune response, or fibrosis have been suggested as being directly or indirectly causative. Many biomechanistic pathways exist for organ failure, and no broad-spectrum curative or preventative compound (agent, active ingredient) has been found.

Viral infection, bacterial infection, or physical injury may cause organ failure. Numerous viruses are known to cause mortality by inducing organ failure in subjects. Such viruses include disseminated herpes simplex virus-1, Ebolavirus, Marburgvirus, coronavirus (CoV), hemorrhagic viruses, filovirus, rabies virus, AIDS/HIV, smallpox virus, influenza virus (A through D), Hanta virus (Hantavirus pulmonary syndrome), Dengue fever virus, rotavirus, SARS-CoV, MERS-CoV, SARS-CoV-2 (COVID-19), Coronavirus 229E, Coronavirus NI63, Coronavirus Oc43, Yellow fever virus, Lassa fever virus, Japanese encephalitis virus, Spanish influenza virus, Hong Kong influenza, Influenza A & B, Parainfluenza 1-4, Adenovirus, Coxsackievirus, Metapneumovirus, Rhinovirus/enterovirus, Respiratory syncytial virus and others. Some of these viruses target particular organs such as the lung, heart, kidney, and/or liver. For example, in influenza virus and SARS-CoV-2 infections, the primary cause of death is pneumonia and severe acute respiratory distress because the viruses target the lungs; however, multiple organ failure is also observed.

The coronavirus disease 2019 (COVID-19) outbreak caused by severe acute respiratory syndrome coronavirus 2 (SARS-CoV-2) is a devastating global health emergency. In addition to COVID-19, the world is continually facing the challenge of seasonal and emergent influenza viruses, and other aggressive viral infections in epidemic proportions on a yearly basis. Irrespective of the origin of viral infection, ARDS and vital organ (including heart, liver, intestine, and kidney) failures are the main cause of morbidity and mortality associated with viral infections. Acute respiratory infections also comprise a large threat for the soldiers and veterans due to exposure, close quarters, and environmental risks. Despite extensive basic and translational research into influenza and coronavirus, a vaccine against coronaviruses has yet to be developed. Moreover, there is not a universal influenza vaccine effective against all influenza virus subtypes due to its high propensity to mutate, requiring seasonal influenza vaccines to be updated annually based on a projection of what strain might be prevalent. The lack of preventive vaccines against these viruses makes emerging influenza and coronaviruses a serious global threat and calls for alternative therapy to treat virus-induced ARDS and multi-organ failures.

Many studies have shown that SARS-CoV predominantly infects airway and alveolar epithelial cells, vascular endothelial cells, and macrophages. The early onset of rapid viral replication may cause massive epithelial and endothelial cell death and vascular leakage, triggering the event of exuberant "inflammatory cytokine storm". In addition, SARS-CoV-2 and/or influenza infection may also cause injury and death of macrophages and lymphocytes, which compromise the innate and adaptive immune responses. Inflammatory cytokine storm-induced tissue injuries are a key contributing factor to respiratory dysfunction and multi-organ failure associated with virus infection. Major clinical manifestations of ARDS, including arterial hypoxemia and pulmonary edema, are direct consequences of the disrupted airway and alveolar barrier function. Therefore, effective ARDS treatment and multi-organ protection requires suppressing the virus-induced inflammatory cytokine storm, resolution of alveolar edema, and most critically the restoration of epithelial and endothelial barrier integrity.

The SARS-CoV-2 virus has the spike protein (S-protein; S1 and S2 proteins), nucleocapsid protein (N-protein; N1 and N2 proteins; phosphoprotein), envelope protein (E-protein), and membrane protein (M-protein; glycoprotein). A compound capable of inhibiting formation, expression and/or proper folding of these proteins may serve as a useful antiviral agent against SARS-CoV-2 infection and COVID-19.

Methods of preparing, isolating, and/or using MG53 (mitsugumin 53; TRIM72) are known: U.S. Pat. No. 7,981,866, WO2008/054561, WO2008/060776, WO2009/073808, WO2010/141810, WO2010/009312, US2011/0202033, US2011/0287004, US2011/0287015, US2013/0123340, WO2011/142744, WO2012/061793, U.S. Pat. Nos. 8,420,338, 8,603,993, 8,603,992, 9,139,630, 9,458,465, 9,494,602, 9,505,821, US2014/0024594, WO2012/134478, WO2012/135868, US2015/0110778, WO2013/036610, US2012/0213737, and WO2016/109638.

U.S. Pat. No. 7,981,866 to Ma suggests that MG53 may have direct antiviral properties; however, the instant inventors have determined, as discussed herein, that MG53 does not have a direct antiviral property (at least in the virus tested herein), because it does not inhibit viral replication in cells infected with influenza virus.

Fibrosis is known to be etiologically related to organ failure. Guo et al. (Exp. Cell Res. (2018), 362(2), 436-443) report that MG53 could induce atrial fibrosis. Chen et al. (J. Cell. Physiol. (2019), 234(10), 17749-17756) report that MG53 causes cardiac fibrosis. Liu et al. (Circ. (2015), 131(9), 795-804) report that cardiac-specific transgenic expression of MG53 induces diabetic cardiomyopathy in mice. Hu et al. (Biochim. Biophys. Acta (2018), 1864(5), part B, 1984-1990) report that sustained upregulation of MG53 disturbs metabolic processes and contributes to the development of muscle metabolic disorders. U.S. Pat. No. 8,383,602 to Kao states that "TRIM72 overexpression inhibits myogenesis" and "the inhibition of TRIM72 acts exclusively on skeletal muscle and heart muscle but does not affect IGF-I signaling pathway in other tissues".

Based upon the above art, the artisan would not expect MG53 to be useful toward preventing, reversing or treating acute or chronic organ failure, and it would be very unexpected to find that MG53 could be used to prevent, reverse or treat viral infection-induced organ failure, be it acute (short-term) or chronic (long-term).

It would be an advancement in the art to provide a method of and composition for preventing, reversing, and/or treating organ failure.

SUMMARY OF THE INVENTION

The present inventors seek to prevent, reverse or treat viral infection-induced organ failure by administration of MG53 or of an MG53-expressing composition. The compositions and dosage forms herein can achieve said goal(s).

One object of the invention is to provide a recombinant human MG53 (rhMG53) protein for preventing, reversing, and/or treating viral infection-induced organ failure. Another object of the invention is to administer said rhMG53 to a subject having a virus infection that induces organ failure. Another object of the invention is to reduce the mortality rate in a population of subjects infected with a virus that induces fatal organ failure. Yet another object of the invention is to mitigate virus infection-induced fibrosis of one or more organs of a subject infected with a virus that induces organ fibrosis. In order to achieve key objectives, the present invention provides the following technical solutions.

An aspect of the invention provides a method of preventing viral infection-induced organ failure, the method comprising administering to a subject, infected with a virus that induces organ failure, one or more doses of MG53, thereby preventing said organ failure. The subject may or may not have contracted said viral infection before administration of MG53.

Another aspect of the invention provides a method of preventing viral infection-induced organ failure, the method comprising administering to a subject, at risk of being infected with a virus that induces organ failure, one or more doses of MG53, thereby preventing said organ failure, said subject not yet having contracted said viral infection prior to administration of MG53.

Another aspect of the invention provides a method of reversing viral infection-induced organ failure, the method comprising administering to a subject, exhibiting (indicated with) viral infection-induced organ failure, one or more doses of MG53, thereby reversing said organ failure. Said subject would have already contracted said viral infection and would already be exhibiting one or more signs/symptoms of failure of one or more organs.

Another aspect of the invention provides a method of reducing the mortality rate in a population of subjects having a viral infection that causes mortality due to organ failure, the method comprising administering to subjects of said population one or more doses of MG53, thereby reducing the mortality rate in said population of subjects.

Another aspect of the invention provides a method of mitigating (e.g. ameliorating, treating, curing) virus-infection induced organ fibrosis, which may or may not be fatal, the method comprising administering to a subject, infected with a virus that induces organ fibrosis, one or more doses of MG53, thereby mitigating fibrosis of one or more organs of said subject.

Another aspect of the invention provides a method of treating COVID-19 (SARS-CoV-2 infection) comprising administering to a subject having a SARS-CoV-2 infection one or more therapeutically effective doses of MG53.

It should be understood that a subject having a SARS-CoV-2 infection might be asymptomatic, meaning the viral infection would not have progressed to COVID-19 disease. COVID-19 is the disease caused by the SARS-CoV-2 virus wherein a subject infected with said virus exhibits one or more symptoms associated with COVID-19, meaning the infected subject is symptomatic.

Another aspect of the invention provides a method of preventing COVID-19 in a subject, the method comprising administering to a subject one or more therapeutically effective doses of MG53, wherein said one or more doses are administered: a) prior to said subject being infected with SARS-CoV-2 virus; orb) within a period of up to five days, up to four days, up to three days, up to two days, or up to one day of said subject having been infected with SARS-CoV-2. In some embodiments, the subject has been in close contact (within six feet) of another subject having SARS-CoV-2 infection.

Another aspect of the invention includes a method of inhibiting expression of a SARS-CoV-2 protein in a tissue or subject infected with SARS-CoV-2 virus, said method comprising administering to said tissue or subject one or more doses of MG53 in an amount sufficient to inhibit said expression. In some embodiments, the protein is the N protein, the E protein, the S protein, and/or the M protein of SARS-CoV-2.

Another aspect of the invention provides a method of treating influenza virus infection comprising administering to a subject having an influenza virus infection one or more therapeutically effective doses of MG53.

Another aspect of the invention provides a method of preventing influenza disease (or influenza virus infection) in a subject, the method comprising administering to a subject one or more therapeutically effective doses of MG53, wherein said one or more doses are administered: a) prior to said subject being infected with influenza virus; orb) within a period of up to five days, up to four days, up to three days, up to two days, or up to one day of said subject having been infected with influenza virus. In some embodiments, the subject has been in close contact (within six feet) of another subject having influenza virus infection.

Another aspect of the invention includes a method of inhibiting expression of an influenza virus protein in a tissue or subject infected with influenza virus, said method comprising administering to said tissue or subject one or more doses of MG53 in an amount sufficient to inhibit said expression. In some embodiments, the protein is the hemagglutinin protein (HA protein), the E protein (envelope protein), the NA protein (neuraminidase protein), M1 protein (matrix protein), and/or the M2 protein (lipid membrane protein) of the influenza virus.

The invention thus provides a method of reducing expression of one or more viral protein(s) in a virus-infected cell, the method comprising administering to said infected cell an effective amount of MG53 sufficient to reduce expression of said one or more viral proteins. The invention thus provides a method of reducing replication of virus in a virus-infected tissue or subject, the method comprising administering to said infected tissue or infected subject an effective amount of MG53 sufficient to reduce replication of said virus.

In some embodiments, said organ failure is short-term or acute organ failure, meaning organ failure that occurs over a period of hours, days, weeks or up to about three months.

In some embodiments, said organ failure is long-term or chronic organ failure, meaning organ failure that occurs over a period of about three months or more.

MG53 can be administered acutely, chronically or a combination thereof. MG53 can be administered according to any dosing regimen that is clinically and/or therapeutically beneficial to a subject receiving it. It can be administered orally, by injection, intravenously, intratracheally, inhalation, nasal spray, aerosol delivery system, nebulizer, intraarterially, subcutaneously, intramuscularly, rectally, by infusion, directly to a target organ, and/or transdermally.

MG53 can be included in any dosage form or kit suitable for administration to a subject in need thereof. Acceptable dosage forms include injectable, intratracheal, oral, peroral, rectal, spray, topical, transdermal, buccal, aerosol delivery system, inhalable, and nebulizer. Such dosage forms exhibit one or more release profiles selected from the group consisting of immediate release, rapid release, extended release, sustained release, controlled release, enteric release, and a combination of any thereof. MG53 may be administered systemically or non-systemically.

The methods of invention can further comprise administration of MG53 and one or more antiviral drug(s) to a subject infected with a virus that induces organ failure. Said antiviral drug(s) may be administered in combination with MG53 or separately from MG53. The administration of MG53 and said one or more antiviral drug(s) can be separate, simultaneous, overlapping or sequential.

The virus that induces organ failure and/or causes mortality can be selected from the group consisting of positive-sense single-stranded RNA virus ((+)-ss-envRNAV), negative-sense single-stranded RNA virus ((−)-ss-envRNAV), double-stranded DNA virus (ds-DNAV), or positive-sense RNA via DNA virus. In some embodiments, the viral infection is caused by any of the following virus families: Arenaviridae, Arteriviridae, Bunyaviridae, Filoviridae, Flaviviridae, Orthomyxoviridae, Paramyxoviridae, Rhabdoviridae, Retroviridae (in particular, Deltaretrovirus genus), Coronaviridae, Togaviridae, Herpesviridae, Poxviridae or Hepadnaviridae.

In some embodiments, the (+)-ss-envRNAV is a virus selected from the group consisting of Coronaviridae family, Flaviviridae family, Togaviridae family, and Arteriviridae family. In some embodiments, the (+)-ss-envRNAV is a coronavirus that is pathogenic to humans. In some embodiments, the coronavirus is selected from the group consisting of SARS-CoV, MERS-CoV, COVID-19 (SARS-CoV-2), CoV 229E, CoV NL63, CoV OC43, CoV HKU1, and CoV HKU20.

In some embodiments, the (+)-ss-envRNAV is a virus selected from the group consisting flavivirus, Yellow Fever virus, Dengue Fever virus, Japanese Enchephalitis virus, West Nile virus, Zikavirus, Tick-borne Encephalitis virus, Kyasanur Forest Disease virus, Alkhurma Disease virus, Omsk Hemorrhagic Fever virus, and Powassan virus.

In some embodiments, the (+)-ss-envRNAV is a Togaviridae family virus selected from the group consisting arbovirus, eastern equine encephalomyelitis virus (EEEV), western equine encephalomyelitis virus (WEEV), Venezuelan equine encephalomyelitis virus (VEEV), Chikungunya virus (CHIKV), O'nyong'nvirus (ONNV), Pogosta disease virus, Sindbis virus, Ross River fever virus (RRV) and Semliki Forest virus.

The invention includes embodiments wherein the viral infection is CoV that is pathogenic to humans, e.g. SARS-CoV, MERS-CoV, COVID-19 (SARS-CoV-2), CoV 229E, CoV NL63, CoV OC43, CoV HKU1, and CoV HKU20.

In some embodiments, the (−)-(ss)-envRNAV is a virus selected from the Arenaviridae family, Bunyaviridae family (Bunyavirales order), Filoviridae family, Orthomyxoviridae family, Paramyxoviridae family, or Rhabdoviridae family.

In some embodiments, Arenaviridae family virus is selected from the group consisting of Lassa virus, aseptic mengitis, Guanarito virus, Junin virus, Lujo virus, Machupo virus, Sabia virus and Whitewater Arroyo virus.

In some embodiments, Bunyaviridae family virus is selected from the group consisting of Hantavirus, and Crimean-Congo hemorrhagic fever orthonairovirus.

In some embodiments, Paramyxoviridae family virus is selected from the group consisting of Mumps virus, Nipah virus, Hendra virus, respiratory syncytial virus (RSV), human parainfluenza virus (HPIV), and NDV.

In some embodiments, Orthomyxoviridae family virus is selected from the group consisting of influenza virus (A through C), Isavirus, Thogotovirus, Quaranjavirus, H1N1 virus, H2N2 virus, H3N2 virus, H1N2 virus, Spanish flu virus, Asian flu virus, Hong Kong Flu virus, and Russian flu virus.

In some embodiments, Rhabdoviridae family virus is selected from the group consisting of rabies virus, vesiculovirus, Lyssavirus, and Cytorhabdovirus.

The organ that undergoes virus infection-induced organ failure can be the respiratory system, heart, lung, kidney, gastrointestinal system and/or liver.

In some embodiments, the composition further comprises one or more zinc salts present in an amount sufficient to stabilize MG53 present in the composition. In a composition of the invention, the molar ratio of Zn ions present to MG53 molecules present is at least 2:1, when considering the two zinc ion binding sites present on each MG53 molecule. In some embodiments, the composition comprises a molar ratio of >2:1 for the moles of Zn to moles of MG53.

In some embodiments, the method of the invention further comprises adjunct administration of with at least one antioxidant, whereby said at least one antioxidant is administered prior to, along with, or after administration of MG53. Accordingly, the method of the invention can further comprise the step of administering at least one antioxidant to a subject. The molar ratio of MG53 to antioxidant can be in the range of 0.01:1 to 10:1.

In some embodiments, a subject is chronically administered MG53, at least one antioxidant, and at least one zinc salt. The invention also provides a composition comprising MG53, at least one antioxidant, and at least one zinc salt. The molar ratio of MG53 to antioxidant can be in the range of 0.01:1 to 10:1.

A composition of the invention can be administered one, two, three or more times per day. It can be administered daily, weekly, monthly, bimonthly, quarterly, semiannually, annually or even longer as needed. It can be administered every other day, five times per week, four times per week, three times per week, two times per week, once daily, twice daily, one to four times daily, continuously, or as frequently or infrequently as needed. The unit dose of each administration is independently selected upon each occurrence from the doses described in this specification or as determined to be therapeutically effective. All combinations of the dosing regimens described are contemplated to be within the scope of the invention.

The composition may be administered one or more times over a treatment period of at least one week. The composition may be administered acutely or chronically. In some embodiments, the chronic administration is at least one weekly, at least once daily, two or more times daily, two or more times per week, or as needed at a dose of about 0.01 mg of MG53/kg of bodyweight to about 10 mg of MG53/kg of bodyweight.

The invention also provides the methods of treatment herein employing an enteric release composition comprising MG53, at least one enteric release material, and one or more pharmaceutical excipients. Following oral or peroral administration, the enteric release composition can be used to deliver MG53 to the gastrointestinal tract of a subject. The invention also provides a method of preventing, reversing or treating viral infection induced organ failure comprising administering to a subject an effective amount of said enteric release composition.

The invention includes all combinations of the aspects, embodiments and sub-embodiments disclosed herein. Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
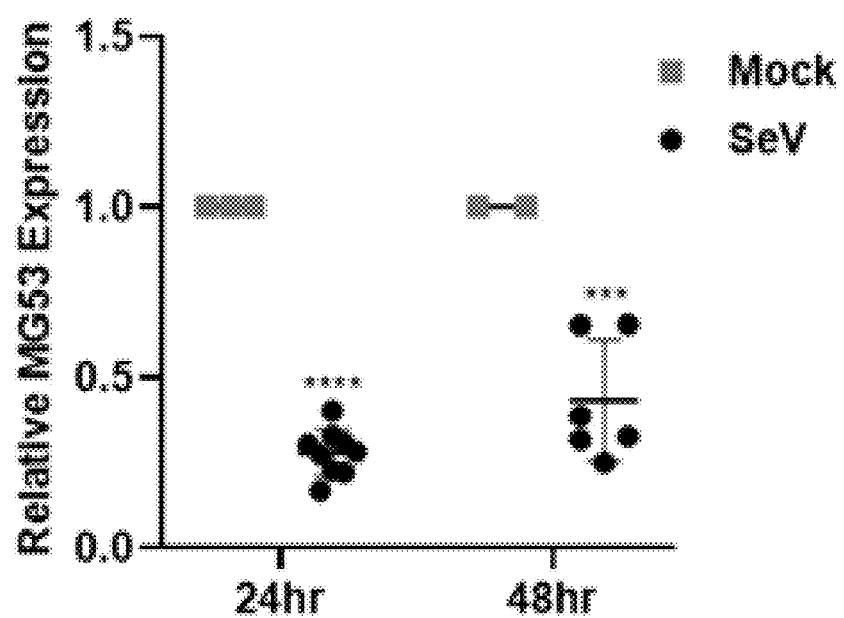
FIG. 1 depicts a chart of the relative expression of MG53 in THP1 cells. Quantification of reduction in MG53 protein expression following SeV infection (data representative of three independent experiments at the 24 h timepoint and two independent experiments at the 48 h timepoint; mean±SD; * $p<0.001$, ** $p<0.0001$; One sample t-tests).

Hereinafter, preferred embodiments of the present invention will be described in detail with reference, as needed, to the accompanying figures.

MG53 protein (also referred to as mitsugumin 53 or TRIM72) is known in the art. Unless specified otherwise, all embodiments of the invention comprising or employing "MG53" include all known forms of MG53. It also refers to recombinant human MG53 (rhMG53). As used herein and unless otherwise specified, the term MG53 (or MG53 protein) refers to the MG53 protein present as the native form, optimized form thereof, mutant thereof, derivative thereof or a combination of any two or more of said forms. Native MG53 contains 477 amino acids that are well conserved in different animal species. Methods of preparing and/or isolating MG53 are known: U.S. Pat. No. 7,981,866, WO2008/054561, WO2009/073808, US2011/0202033, US2011/0287004, US2011/0287015, US2013/0123340, WO2011/142744, WO2012/061793, U.S. Pat. Nos. 8,420,338, 9,139,630, 9,458,465, 9,494,602, US2014/0024594, WO2012/134478, WO2012/135868, US2015/0110778, WO2013/036610, US2012/0213737, WO2016/109638, the entire disclosures of which, including sequence information therein, are hereby incorporated by reference.

The sequence listing information for native MG53, and variants or various forms thereof, is disclosed in U.S. Pat. Nos. 7,981,866 and 9,139,630, the entire disclosures of which, including sequence information therein, are hereby incorporated by reference. The sequence listing information for a cDNA that encodes optimized native human MG53, or a fragment thereof, is disclosed in U.S. Pat. No. 9,139,630, the entire disclosure of which, including sequence information therein, is hereby incorporated by reference.

As used herein in reference to MG53, the term "mutant" means a recombinant form of MG53 having an amino acid change (replacement) of one, two, three or more amino acids in the amino acid sequence of native MG53. Mutant forms of MG53 and methods of preparing the same are known: US2015/0361146, EP3118317, WO2015/131728, U.S. Pat. No. 9,139,630, the entire disclosures of which, including sequence information therein, are hereby incorporated by reference.

As used herein the term "endogenous MG53", refers to MG53 present in a subject prior to treatment with a composition or method according to the invention. As used herein, exogenous MG53 is nonendogenous MG53.

As used herein, a subject at risk of viral infection is: a) a subject living in a geographical area within which mosquitos, in particular *Aedes* species (*Aedes egypti, Aedes albopictus*) mosquitos, live; b) a subject living with or near a person or people having viral infection; c) a subject having sexual relations with a person having a viral infection; d) a subject living in a geographical area within which ticks, in particular *Ixodes* species (*Ixodes marx, Ixodes scapularis*, or *Ixodes cooke* species) ticks, live; e) a subject living in a geographical area within which fruit bats live; f) subjects living in a tropical region; g) subjects living in Africa; h) subjects in contact with bodily fluids of other subjects having a viral infection; i) a child; or j) a subject with a weakened immune system. In some embodiments, the subject is a female, a female capable of getting pregnant, or a pregnant female.

As used herein, the term "subject" is taken to mean warm blooded creatures such as mammals, for example, cats, dogs, mice, guinea pigs, horses, bovine cows, sheep, and humans.

The present inventors have unexpectedly discovered that virus infection-induced organ failure can be prevented, reversed or treated by administration of MG53 to a subject having a virus infection that causes organ failure.

An in vitro viral assay was developed (Example 1) to determine whether MG53 expression is altered in THP1 cells upon infection with SeV (Sendai virus). We observed that SeV infection reduced MG53 protein expression by more than 50% (FIG. 1). This suggests that MG53 levels in cells are decreased during certain viral infections.

Figure 2:
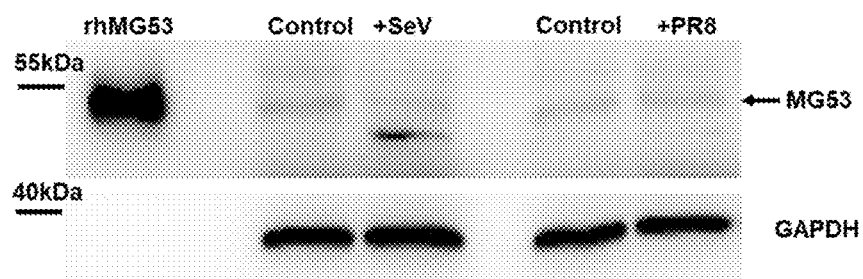
FIG. 2. depicts a photograph of a gel comparing the effect of Sendai virus (SeV) and influenza virus H1N1 strain PR8 infection upon MG53 expression in THP1 cells.

We then compared the effects of SeV and influenza H1N1 strain PR8 infection on MG53 expression in THP1 cells (Example 2). We observed that SeV infection consistently led to reduced MG53 protein levels in THP1 cells, but influenza infection did not appear to induce a significant decrease in MG53 in THP1 cells (FIG. 2). This demonstrates that alterations in MG53 levels is virus-specific and suggests that certain viruses may manipulate MG53 levels.

Figure 3:
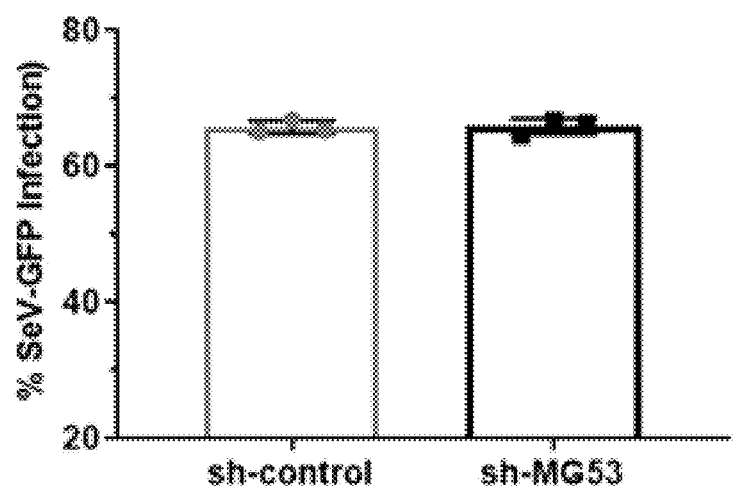
FIG. 3 depicts a chart of the percentage of SeV-GFP (green fluorescent protein labelled SeV) positive cells. Quantification of percentage of SeV-GFP positive cells (data representative of 4 independent experiments; mean±SD; unpaired t-test).

We then determined whether endogenous MG53 affects the infection rate of cells by SeV (Example 3). shRNA was used to knock down the expression of MG53 in THP1 cells and, in doing so, confirmed that MG53 is also expressed in undifferentiated THP1 cells. Control shRNA (sh-control) and sh-MG53 knockdown THP1 cells were infected with SeV expressing GFP for 24 h. Cells were collected and examined by flow cytometry for GFP fluorescence, indicative of virus infection and virus protein production. We observed that knockdown of MG53 did not significantly affect the percentage of cells infected with virus as compared to sh-control cells, thereby indicating similar infection rates of sh-MG53 and sh-control THP1 cells (FIG. 3). This is indicative of the absence of a direct antiviral effect by MG53.

Figure 4A:
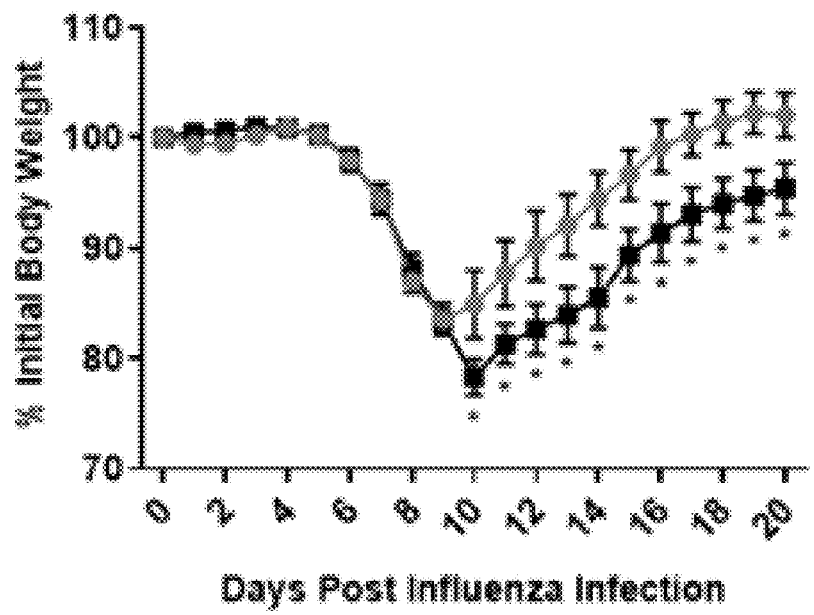
FIG. 4A depicts a chart of the percentage of initial body weight over time for mice infected with influenza virus. Mice were infected intranasally with influenza virus PR8 (10 TCID50). MG53 KO mice lost more weight and took longer to recover following PR8 infection compared to controls (n=12 mice/group, mean±SE; *=$p<0.05$; Multiple t-tests).

We then determined whether MG53 plays a physiological role during in vivo viral infection, MG53 wild type (WT) and knockout (KO) mice were intranasally infected with influenza virus strain PR8 at a dose of 10 tissue culture infectious dose 50 (TCID50) (Example 4). This dose causes weight loss in WT mice, peaking around day 10, followed by a full recovery of body weight. Even though MG53 has no direct antiviral activity, we observed in MG53 KO mice a more severe decrease in weight following infection and a delayed recovery compared to WT mice (FIG. 4A). This suggests that MG53 provides defense against morbidity during respiratory infection with influenza virus.

Figure 4B:
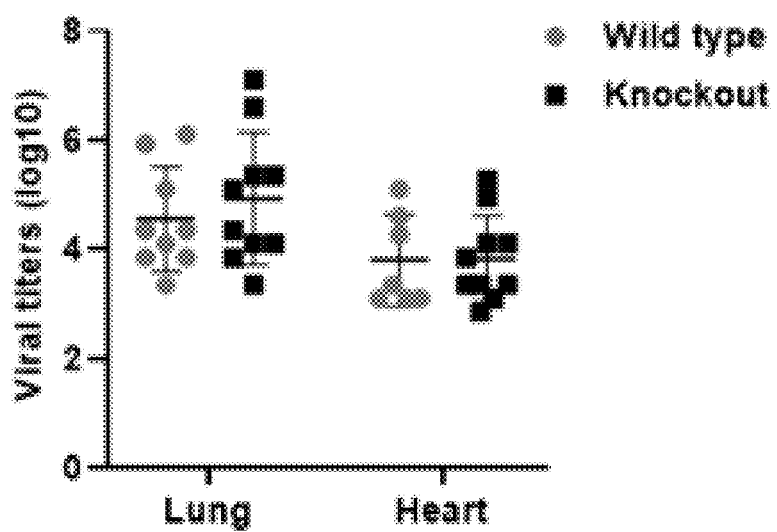
FIG. 4B depicts a chart of the viral titer in lung and heart tissue of wild type (WT) and knockout (KO) mice five days after infection with influenza virus. Lung and heart tissues were harvested from mice 5 days post infection. There was no significant difference in viral burden, as shown by comparable viral titers between WT and KO mice (n=9 WT mice and 10 KO mice; mean±SE; unpaired t-test). Lungs were isolated at 5 days post infection and either fixed for histology or homogenized for viral titer.

We then determined whether differences in virus replication and dissemination were responsible for worsened morbidity in KO mice. Virus titers were measured from lung and heart tissues 5 days post infection. WT and KO mice showed no significant difference in virus titers across tissues (FIG. 4B), suggesting comparable levels of viral replication and dissemination at this time point post infection. This is further evidence that MG53 does not possess a direct antiviral effect.

Figure 5:
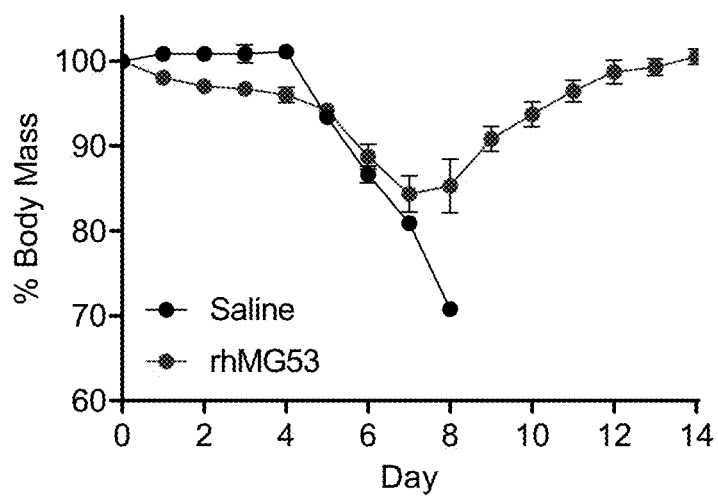
FIG. 5 depicts a graph of percent body mass versus time (day) for WT C57BL/6J mice (8 week old Jackson laboratories) intranasally infected with 100 TCID50 Influenza A virus PR8 in 50 ul sterile saline, then intravenously treated with saline as control and rhMG53 (2 mg/kg, in saline). See Example 5. Mice were monitored daily for (A) body mass and (B) survival. All untreated infected mice lost weight until death (see FIG. 6); whereas all treated infected mice lost weight during the first half of the 2-week study period but ultimately regained full body weight by the end of the 2-week study period.

We then determined whether exogenously administered MG53 might decrease mortality in mice infected with a lethal dose of influenza virus (Example 5). The mice were divided into two groups with each group receiving the same dose of influenza virus (100 TCID50 influenza A virus H1N1 strain PR8. The control group was not administered MG53, and the test group was administered exogenous MG53 (dose: 2 mg/kg). The body weight of the mice was monitored (FIG. 5).

Figure 6:
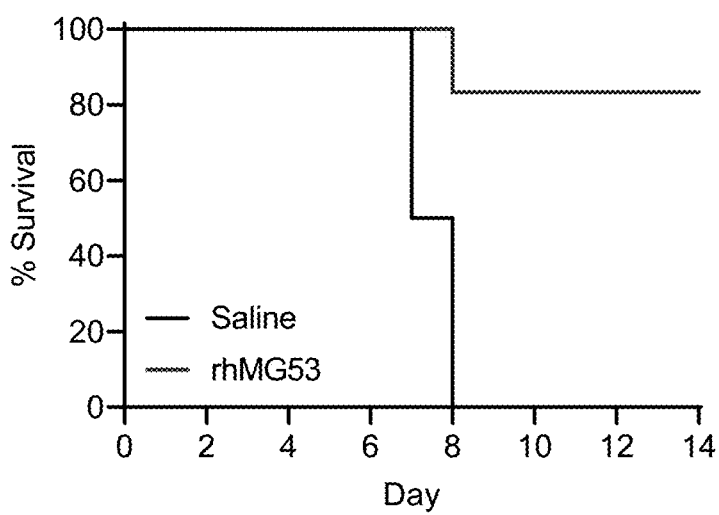
FIG. 6 depicts a graph of the survival rate of the mice of FIG. 5. All untreated infected mice died by day-8; whereas almost all treated infected mice survived beyond the 2-week endpoint of the study.

After 8 days, all of the untreated mice had died, and all of the treated mice survived (FIG. 6). By day-14, all of the treated mice had completely recovered. Bodyweight of those mice was also recorded (FIG. 5). The treated mice were then euthanized. Post-mortem examination of the lung and heart of control and test mice was conducted. It was determined that the untreated control mice died of organ failure.

Figure 7:
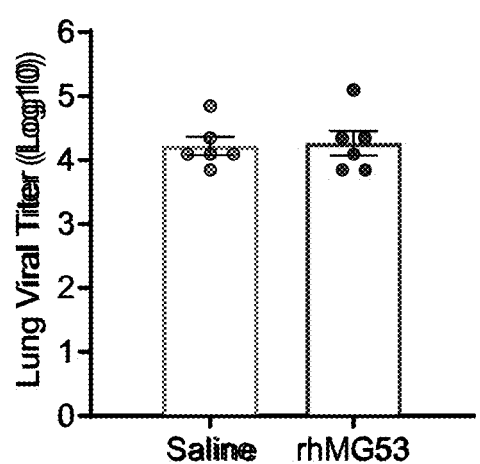
FIG. 7 depicts a chart of the viral titer of TCID50 in the lung tissue of the mice of FIG. 5 at day 7 post infection. There was no substantial difference in viral titer between treated and untreated infected mice.

The viral TCID50 titer for the lung tissue of all mice was calculated using the classic Reed & Muench method. Data demonstrated that saline and rhMG53 treated mice exhibited the same viral titer in the lung tissue (FIG. 7). This indicates that MG53 does not possess direct antiviral activity.

Figure 8:
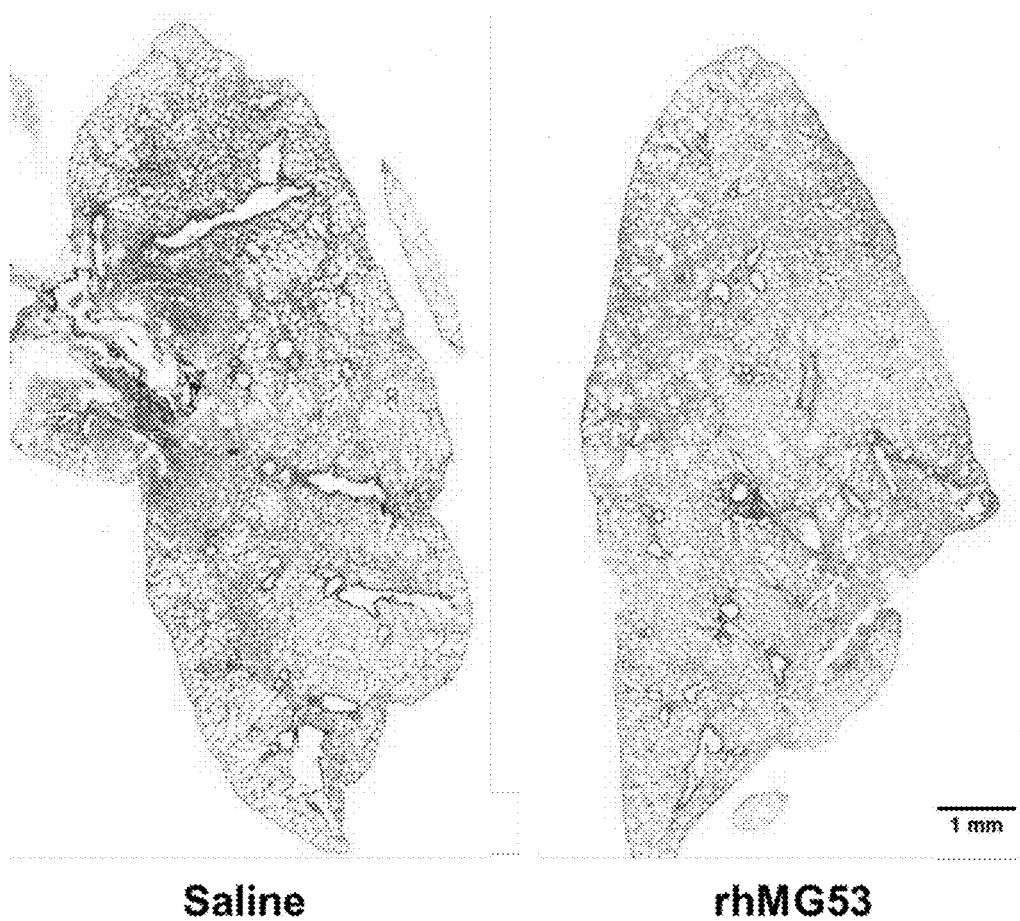
FIG. 8 depicts photographs of lung tissue after Trichrome staining after the mice of FIG. 5 were euthanized and lung tissues were collected. The Trichrome staining showed the extent of fibrosis (stained blue lesions) in the lungs. rhMG53 treatment (right) reduced the formation of viral infection-induced fibrosis as compared to saline control (left).

Lungs were collected from the euthanized mice and stored in 4% PFA for histological analysis. Lung tissue Trichrome staining (Example 13) showed the lungs derived from mice treated with rhMG53 (FIG. 8: right) have less viral infection-induced fibrosis as compared to untreated saline control mice (FIG. 8: left).

Since SARS-CoV-2 virus, in COVID-19 disease, primarily (albeit not solely) targets pulmonary tissue, and SARS-CoV-2 virus is constructed of M protein, E protein, S protein and N protein, we evaluated the impact of MG53 administration upon expression of the proteins and their respective RNAs. If MG53 were to cause a reduction in expression of any of those proteins or RNAs, then MG53 would be exhibiting a direct antiviral activity beyond any reparative property it may have. Such antiviral activity, particularly against SARS-CoV-2 infection has not been disclosed or suggested in the art.

Figure 9:
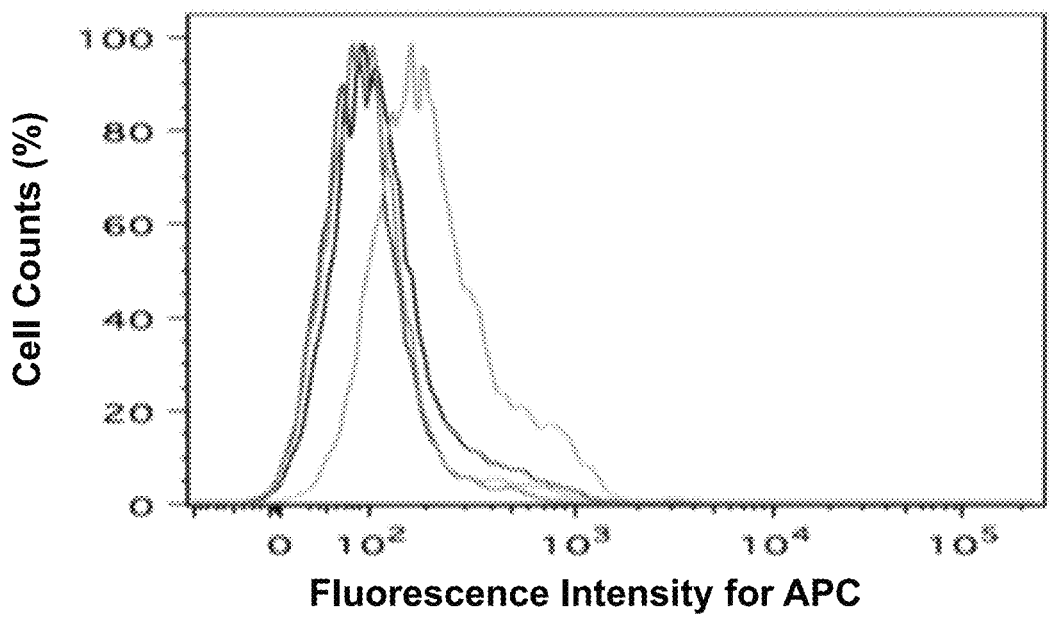
FIG. 9 depicts a histogram of the FACS (fluorescence-activate cell sorting) analysis of A549 cells (adenocarcinomic human alveolar basal epithelial cells) with stable expression of hACE2-GFP (human angiotensin-converting enzyme 2 labeled with green fluorescent protein) infected or not infected with SARS-CoV-2 and treated or not treated with MG53 (Example 15).
Figure 10:
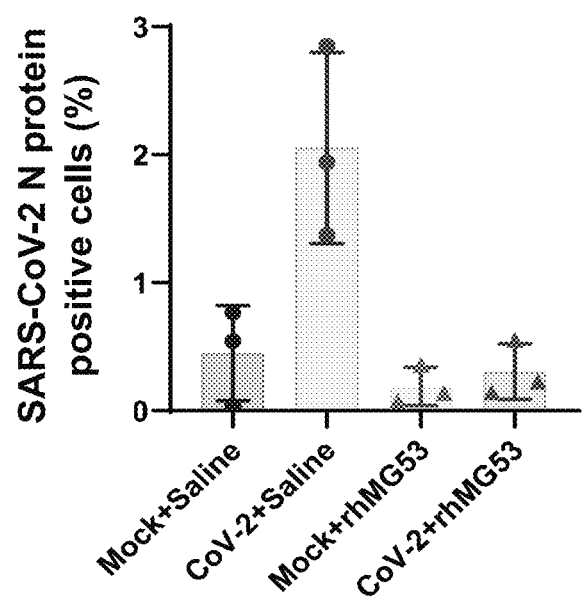
FIG. 10 depicts a chart of the number of SARS-CoV-2 N protein positive cells for the samples of FIG. 9.

Per the example herein, we evaluated the impact of MG53 upon formation of SARS-C-oV-2 N protein positive A549 cells. The data in FIG. 9 (Example 15) indicates that the histogram of FACS data were overlapped, suggesting the reduction or left shift of SARS-CoV-2 nuclear (N) protein positive cells in the group of treated with both SARS-CoV-2 and rhMG53 (orange) compared to cells infected with SARS-CoV-2 only. The quantitative analysis was shown in FIG. 10, indicating the significant decrease of SARS-CoV-2 nuclear (N) protein positive cells upon the treatment with 10 µg/ml rhMG53 (p=0.0177).

Figure 11:
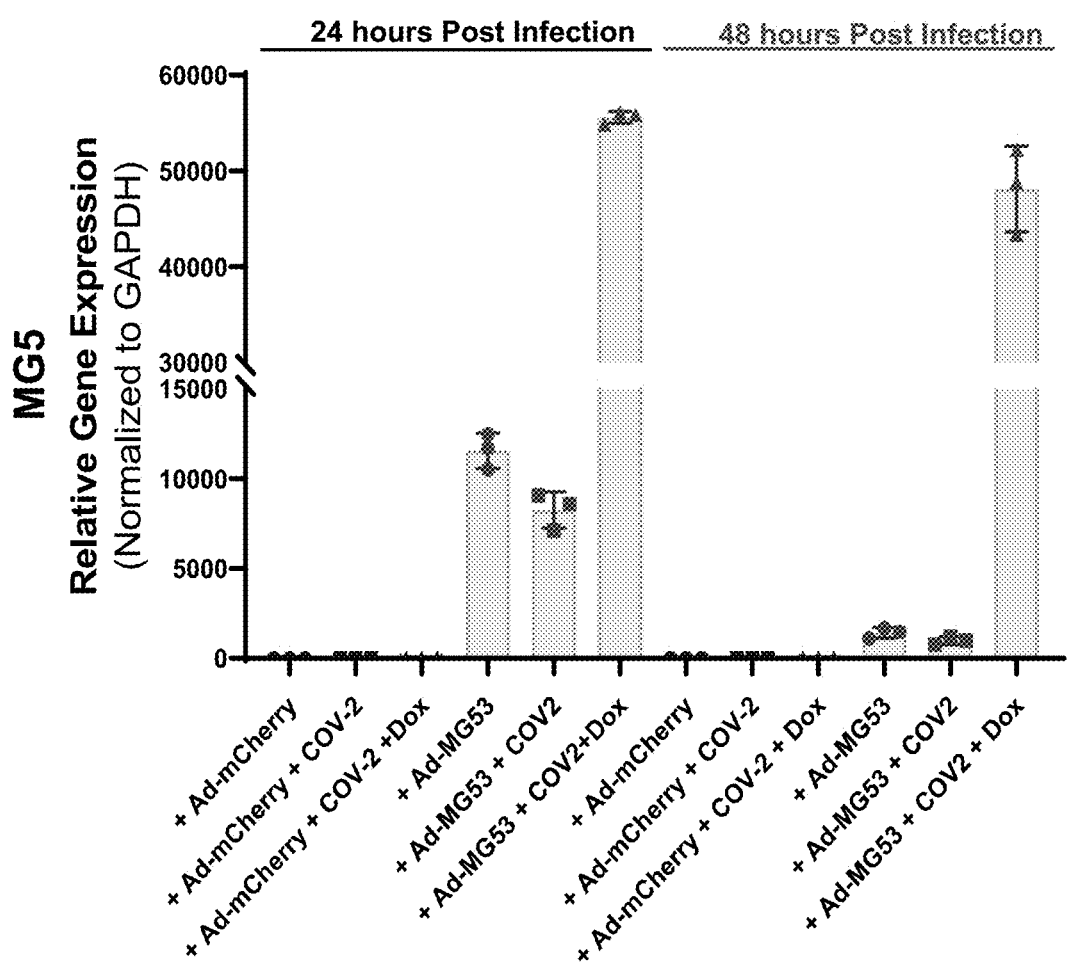
FIG. 11 depicts a chart of the relative expression of the MG53 gene (normalized to GAPDH) in BEAS-2B cells (normal bronchial epithelial cells infected with adenovirus expressing MG53 or vector) infected or not infected with SARS-CoV-2, treated or not treated with MG53 (Example 16).
Figure 12:
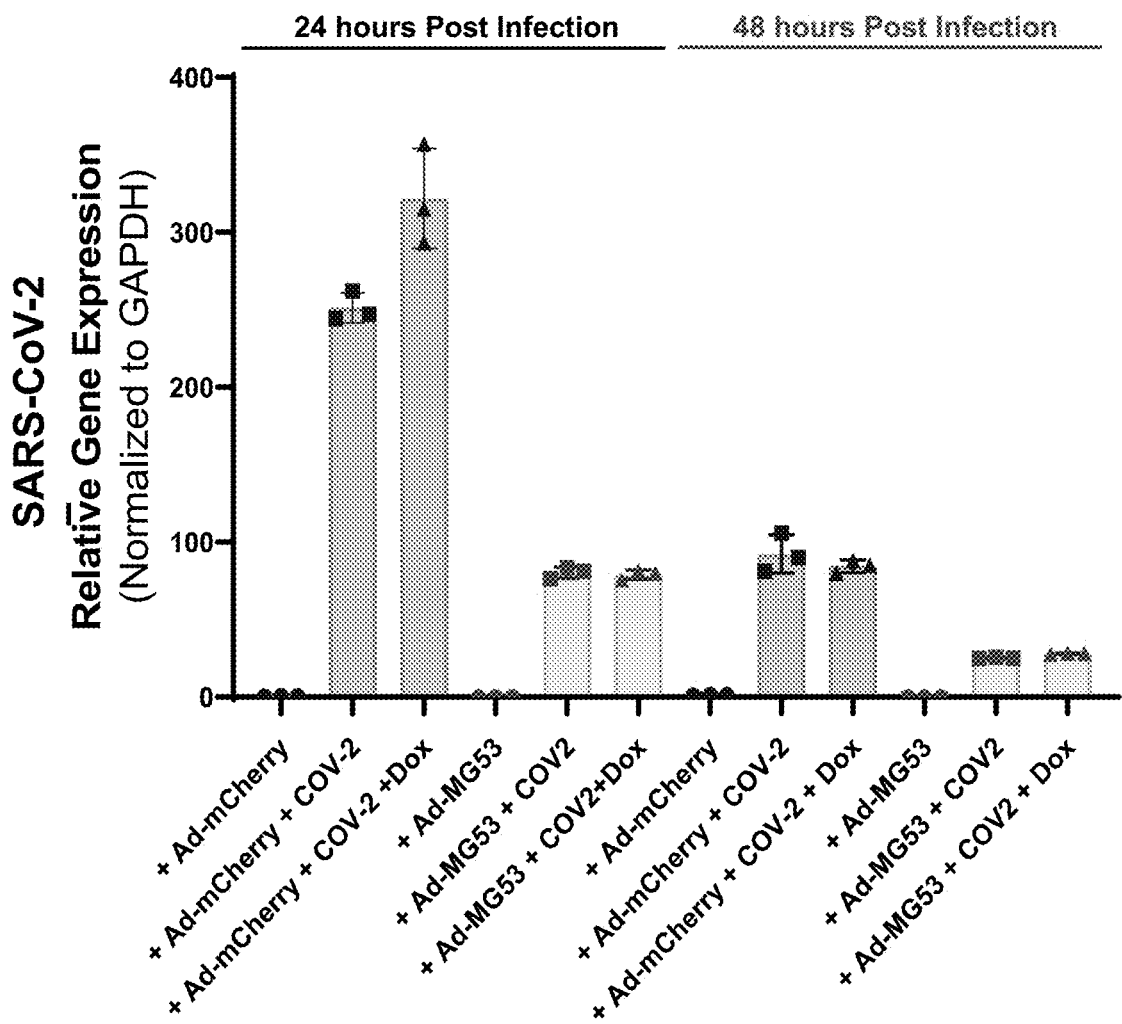
FIG. 12 depicts a chart of the relative expression of the SARS-CoV-2 E protein gene (normalized to GAPDH) for the BEAS-2B cells of FIG. 11.
Figure 13:
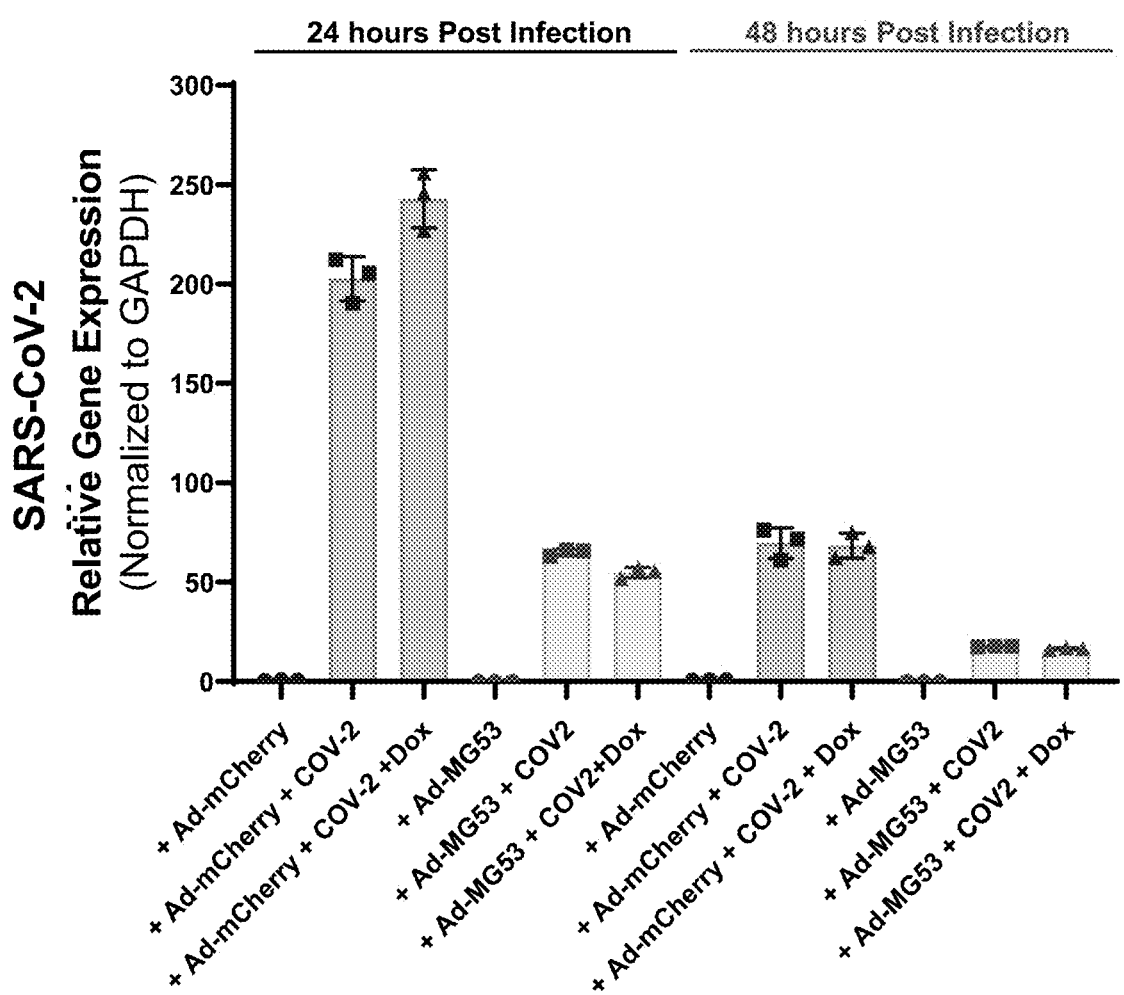
FIG. 13 depicts a chart of the relative expression of the SARS-CoV-2 N1 protein gene (normalized to GAPDH) for the BEAS-2B cells of FIG. 11.

We also evaluated the impact of MG53 upon formation of SARS-C-oV-2 E protein, N1 protein, and N2 protein in positive BEAS-2B cells (Example 16). The level of MG53 gene expression in BEAS-2B cells infected with adenovirus expressing MG53 or vector as control was determined. The BEAS-2B cells were also infected with SARS-CoV-2 virus. The data in FIG. 11 confirms robust expression of MG53 at 24 and 48 hours post SARS-CoV-2 infection. The expression of MG53 is leaked due to low level of doxycycline (DOX) or its homolog in the cell culture medium and is largely induced by the treatment of 1 µM doxycycline. The results shown in FIGS. 12-14 indicate that expression of the genes for the E-protein, N1-protein, and N2-protein of the SARS-CoV-2 virus is significantly suppressed upon the expression of MG53 in BEAS-2B cells. Expression of MG53 in the infected cells resulted in reduced expression of the viral proteins at 24 and 48 hours post SARS-CoV-2 infection and was even able to overcome the DOX-induced increased expression of the viral proteins.

The invention thus provides a method of reducing expression of one or more viral protein(s) in a virus-infected cell, the method comprising administering to said infected cell an effective amount of MG53 sufficient to reduce expression of said one or more viral proteins. The invention thus provides a method of reducing replication of virus in a virus-infected tissue or subject, the method comprising administering to said infected tissue or infected subject an effective amount of MG53 sufficient to reduce replication of said virus. In some embodiments, a) the virus is an enveloped virus; b) the viral protein is selected from the group consisting of envelope protein, nuclear (perinuclear) protein, or a combination thereof; c) the virus is selected from the group consisting of influenza virus and SARS-CoV-2 virus; d) the virus is selected from a virus family selected from the group consisting of Arenaviridae, Arteriviridae, Bunyaviridae, Filoviridae, Flaviviridae, Orthomyxoviridae, Paramyxoviridae, Rhabdoviridae, Retroviridae (in particular, Deltaretrovirus genus), Coronaviridae, Togaviridae, Herpesviridae, Poxviridae and Hepadnaviridae (said families, genera, and species being as defined herein); e) the coronavirus is selected from the group consisting of SARS-CoV, MERS-CoV, COVID-19 (SARS-CoV-2), CoV 229E, CoV NL63, CoV OC43, CoV HKU1, and CoV HKU20; f) the virus is an enveloped virus selected from the group consisting of (−)-(ss)-envRNAV and (+)-(ss)-envRNAV; and g) a combination of any two or more of the above.

Figure 15:
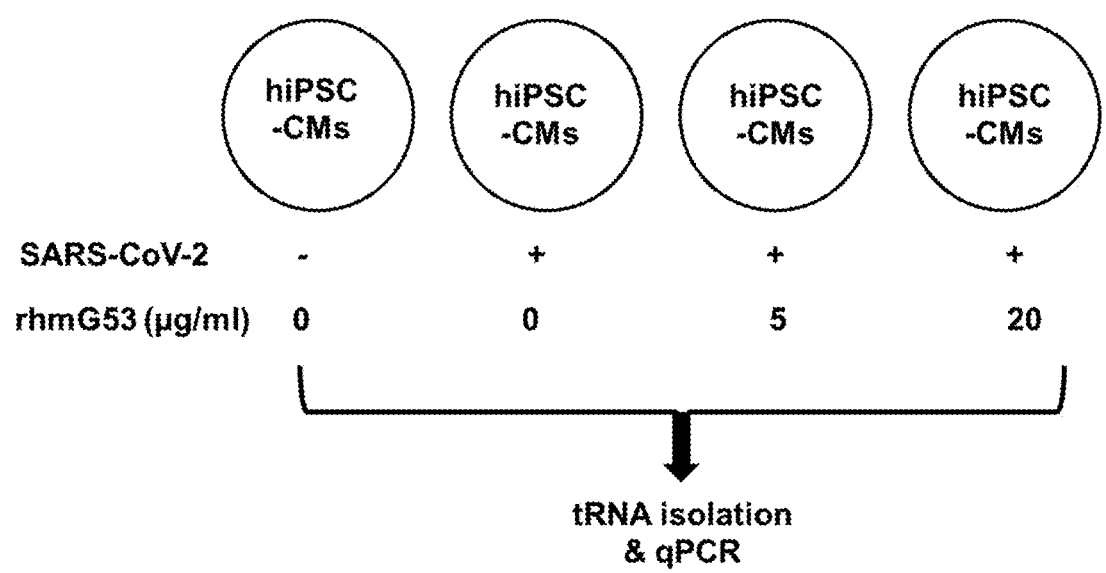
FIG. 15 depicts a diagram of the protocol used to infect beating hiPSC-CMs (human induced pluripotent stem cell-derived cardiomyocytes) with SARS-CoV-2 followed by treatment (or not) with MG53 (Example 17).
Figure 16:
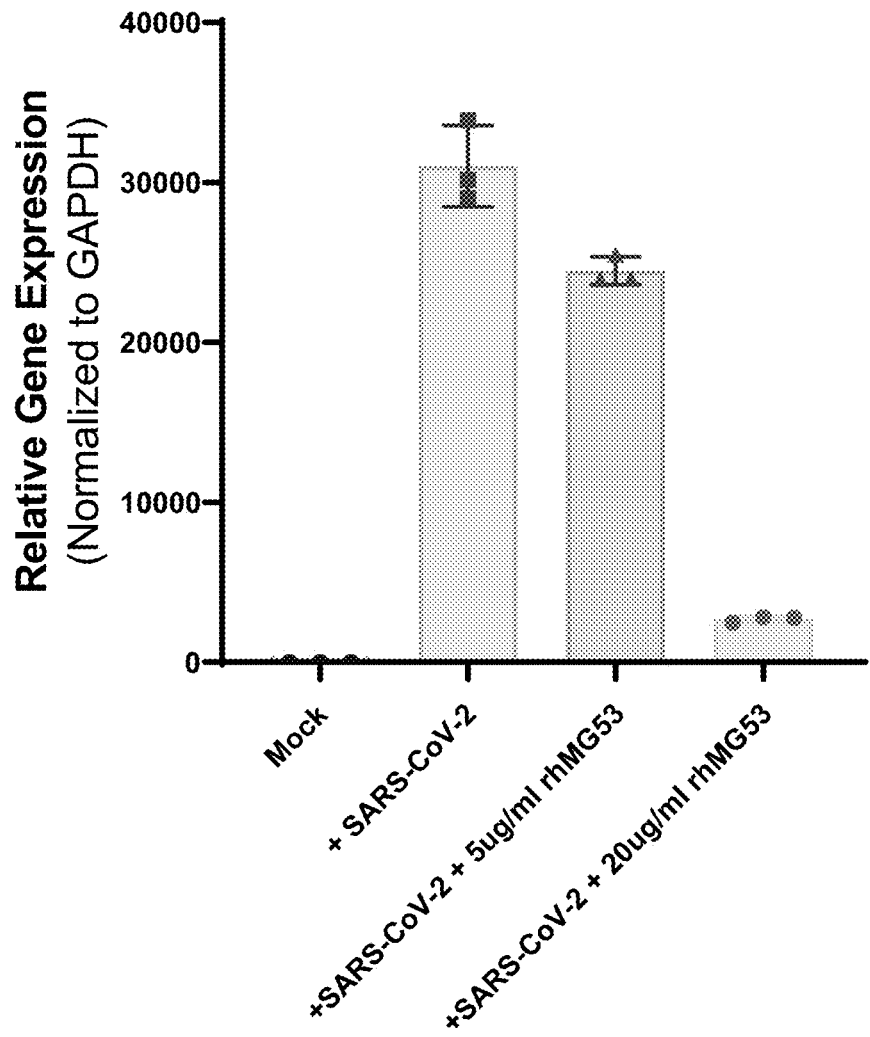
FIG. 16 depicts a chart of the relative expression of the SARS-CoV-2 E protein gene (normalized to GAPDH) for the hiPSC-CMs of FIG. 15.
Figure 17:
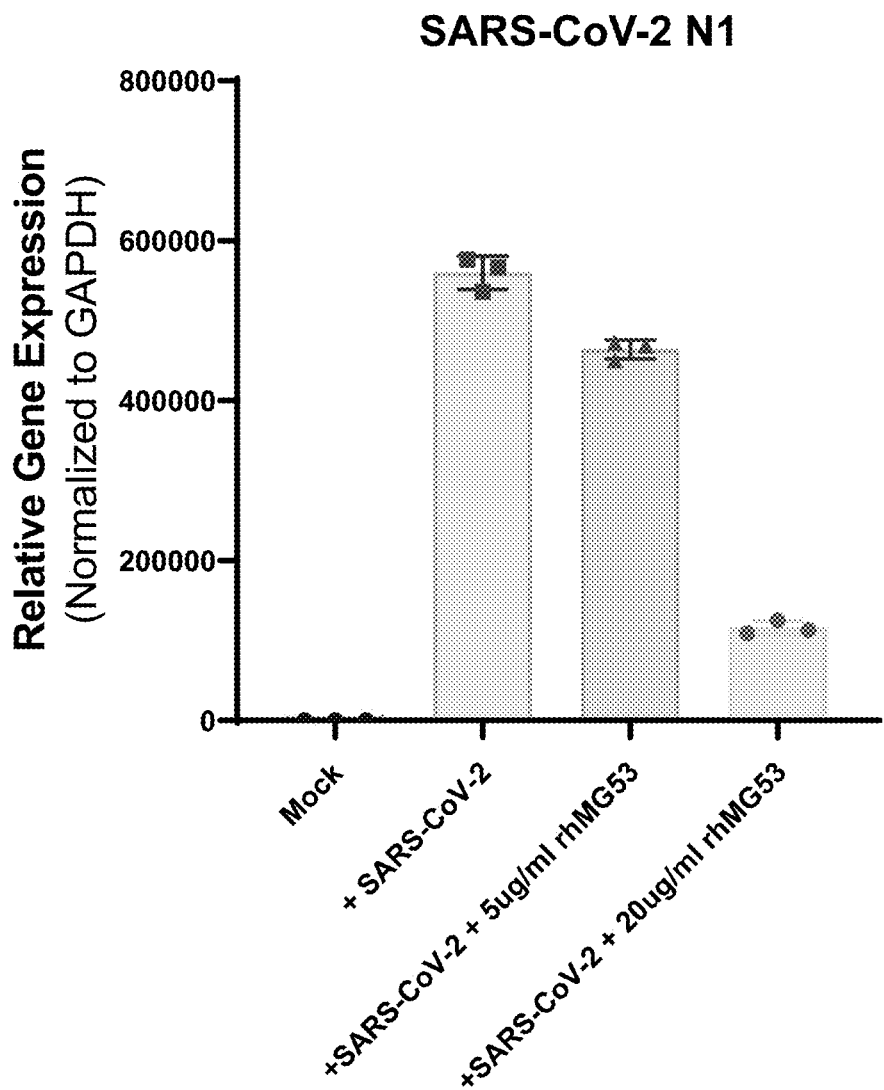
FIG. 17 depicts a chart of the relative expression of the SARS-CoV-2 N1 protein gene (normalized to GAPDH) for the hiPSC-CMs of FIG. 15.
Figure 18:
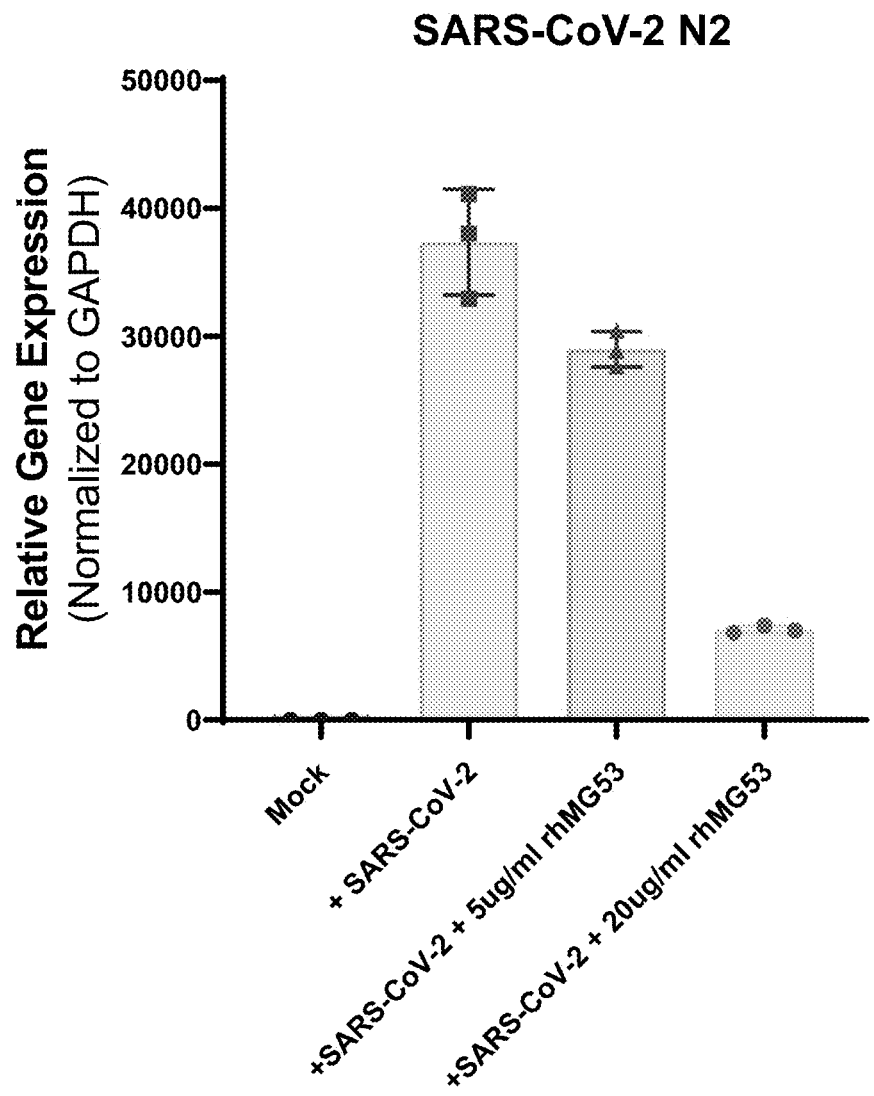
FIG. 18 depicts a chart of the relative expression of the SARS-CoV-2 N2 protein gene (normalized to GAPDH) for the hiPSC-CMs of FIG. 15.

The impact of MG53 upon the relative gene expression for viral proteins in cardiomyocytes infected with SARS-CoV-2 was evaluated according to Example 17 using the protocol detailed in FIG. 15. Beating hiPSC-CMs (human induced pluripotent stem cell-derived cardiomyocytes) were infected with SARS-CoV-2 and treated with solutions containing different concentrations of MG53 (5 microg/mL and 20 microg/mL). Importantly, infected mycocytes that were not treated with MG53 did not continue beating due to failure caused by the viral infection; however, infected myocytes that were treated with MG53 continue to beat. Results from the qPCR showed the SARS-CoV-2 viral level is significantly suppressed upon the treatment with rhMG53 in the concentration dependent manner in hiPSC-CMs. The data depicted in FIGS. 16-18 indicate that administration of MG53 was effective at suppressing expression of the E-protein, N1-protein, and N2-protein by at least 4-fold, at least 5-fold, at least 6-fold, or at least 7-fold. The data also evidences the fact that MG53 is surprisingly exhibiting direct antiviral activity, since it is able to stop progression of a SARS-CoV-2 infection to COVID-19, which progression otherwise results in organ failure, which in this case would be cardiac failure.

Since viral infection may induce long-term (chronic) organ failure by fibrosis, the invention also provides a method of mitigating viral infection-induced organ fibrosis, which might or might not be fatal. Contrary to what is suggested in the art, administration of exogenous MG53 is useful for preventing, reversing or treating long-term organ failure, in particular for mitigating viral infection induced organ fibrosis. A subject having a viral infection that induces organ fibrosis is administered MG53 according to a dosing regimen as described herein. As a result, virus infection-induced fibrosis in the subject's organ is reduced (reversed) or progression of fibrosis is slowed or delayed compared to what might be expected (based upon comparison to an average population of subjects having said viral infection) had the subject not been administered MG53.

The invention thus provides a method of preventing, reversing or treating organ failure, in particularly short-term or acute organ failure, in a subject infected with a virus that causes said organ failure. It also provides a method reducing the mortality rate in a population of subjects infected with a virus that causes said organ failure. It also provides a method of mitigating or reducing viral infection-induced organ fibrosis in a subject infected with a virus that causes organ fibrosis.

If a clinician intends to treat a subject with a combination of MG53 (MG53-containing composition) and one or more other antiviral agents, and it is known that the organ failure-inducing viral infection, which the subject has, is at least partially therapeutically responsive to treatment with said one or more other antiviral agents, then the present method invention comprises: administering to the subject in need thereof a therapeutically relevant dose of MG53 (MG53-containing composition or MG-53-expressing composition) and a therapeutically relevant dose of said one or more other antiviral agents, wherein the MG53 is administered according to a first dosing regimen and the one or more other antiviral agents is administered according to a second dosing regimen. In some embodiments, the first and second dosing regimens are the same. In some embodiments, the first and second dosing regimens are different.

Methods of the invention include separate administration or coadministration of the MG53 with at least one other known antiviral composition, meaning the MG53 can be administered before, during or after administration of a known antiviral composition. In some embodiments, a composition for treating symptoms associated with the viral infection can also be administered to the subject to which MG53 is being administered. For example, medications used to treat inflammation, vomiting, nausea, headache, fever, diarrhea, nausea, hives, conjunctivitis, malaise, muscle pain, joint pain, seizure, or paralysis can be administered with or separately from the antiviral composition of the invention.

The one or more other antiviral agents can be administered at doses and according to dosing regimens that are clinician-recognized as being therapeutically effective or at doses that are clinician-recognized as being sub-therapeutically effective. The clinical benefit and/or therapeutic effect provided by administration of a combination of MG53 and one or more other antiviral agents can be additive or synergistic, such level of benefit or effect being determined by comparison of administration of the combination to administration of the individual MG53 and one or more other antiviral agents. The one or more other antiviral agents can be administered at doses and according to dosing regimens as suggested or described by the Food and Drug Administration, World Health Organization, European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

Exemplary other antiviral agents that can be included in the method (and/or composition) of the invention for the treatment of viral infection-induced organ failure include antiretroviral agent, interferon alpha (IFN-a), zidovudine, lamivudine, cyclosporine A, CHOP with arsenic trioxide, sodium valproate, methotrexate, azathioprine, one or more symptom alleviating drug(s), steroid sparing drug, corticosteroid, cyclophosphamide, immunosuppressant, anti-inflammatory agent, Janus kinase inhibitor, tofacitinib, calcineurin inhibitor, tacrolimus, mTOR inhibitor, sirolimus, everolimus, IMDH inhibitor, azathioprine, leflunomide, mycophenolate, biologic, abatacept, adalimumab, anakinra, certolizumab, etanercept, golimumab, infliximab, ixekizumab, natalizumab, rituximab, secukinumab, tocilizumab, ustekinumab, vedolizumab, monoclonal antibody, basilix-imab, daclizumab, polyclonal antibody, nucleoside analogs, reverse transcriptase inhibitor, emtricitabine, telbivudine, abacavir, adefovir, didanosine, emtricitabine, entecavir, stavudine, tenofovir, azithromycin, macrolide-type antibiotic, protease inhibitor, interferon, immune response modifier, mRNA synthesis inhibitor, protein synthesis, inhibitor, thiazolide, CYP3A4 inhibitor, heterocyclic biguanidine, CCR5 receptor inhibitor, and combinations thereof. Therapies studied also include plasmapheresis and/or radiation. Antibodies to specific viruses may also be administered to a subject treated with the antiviral composition of the invention. Plasma obtained from the blood of survivors of a first viral infection can be administered to other subjects having the same type of viral infection, said other subjects also being administered the antiviral composition of the invention. For example, the plasma from a survivor of COVID-19 infection may be administered to another subject having a COVID-19 infection, said other subject also being administered the MG53 composition of the invention.

MG53 may be administered to a subject in many different forms.

Since MG53 can be degraded by proteases in the GI tract or by the acidic conditions of the stomach, MG53 may be administered a probiotic composition whereby a safe microbe is engineered to express MG53. The probiotic composition is then administered orally (perorally) to a subject such that the microbe expresses MG53 in the GI tract of a subject. Exemplary probiotic compositions are disclosed in international application No. PCT/US2019/060684 to Ma, the entire disclosure of which is hereby incorporated by reference.

As another means of providing MG53 to the intestinal tract downstream of the stomach, an enteric release (ER) composition comprising MG53 was developed. The ER composition comprises MG53, an enteric release pharmaceutical excipient, and a cyclodextrin. In particular embodiments, the ER composition comprises MG53, at least one enteric release polymer, and at least one cyclodextrin derivative.

In particular embodiments, the enteric release polymer is a copolymer of methacrylic acid and methyl methacrylate. In particular embodiments, the enteric release polymer has a dissolution pH of ≥about 5, ≥about 5.5, ≥about 6, ≥about 6.5, or ≥about 7.

In particular embodiments, the cyclodextrin derivative is water soluble. In particular embodiments, the cyclodextrin derivative is hydroxypropyl-beta-cyclodextrin.

The amount of therapeutic compound (MG53) incorporated in each dosage form will be at least one or more unit doses and can be selected according to known principles of pharmacy. An effective amount of therapeutic compound is specifically contemplated. By the term "effective amount", it is understood that, with respect to, for example, pharmaceuticals, a pharmaceutically (therapeutically) effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient.

Suitable concentrations of MG53 in a liquid dosage form include at least 1 ng of MG53/ml, at least 5 ng of MG53/ml, at least 10 ng of MG53/ml, at least 25 ng of MG53/ml, at least 50 ng of MG53/ml, at least 75 ng of MG53/ml, at least 100 ng of MG53/ml, at least 250 ng of MG53/ml, at least 500 ng of MG53/ml, at least 750 ng of MG53/ml, at least 1 microg of MG53/ml, at least 5 microg of MG53/ml, at least 10 microg of MG53/ml, at least 15 microg of MG53/ml, at least 20 microg of MG53/ml, at least 25 microg of MG53/ml, at least 30 microg of MG53/ml, at least 50 microg of MG53/ml, or at least 100 microg of MG53/ml. Higher concentrations are also acceptable, particularly in view the efficacy dose-response trend observed for MG53. These doses can be administered on a frequency as described herein or as determined to be most effective.

A dosing regimen includes a therapeutically relevant dose (or effective dose) of MG53 administered according to a dosing schedule. A therapeutically relevant dose, therefore, is a therapeutic dose at which a therapeutic response of the organ failure to treatment with a composition as described is observed and at which a subject can be administered said composition without an excessive amount of unwanted or deleterious side effects. A therapeutically relevant dose is non-lethal to a subject, even though it may cause some side effects in the patient. It is a dose at which the level of clinical benefit to a subject being administered said composition exceeds the level of deleterious side effects experienced by the subject due to administration of said composition or component(s) thereof. A therapeutically relevant dose will vary from subject to subject according to a variety of established pharmacologic, pharmacodynamic and pharmacokinetic principles.

A therapeutically relevant dose can be administered according to any dosing regimen typically used in the treatment of viral infection. A therapeutically relevant dose can be administered once, twice, thrice or more daily. It can be administered every other day, every third day, every fourth day, every fifth day, semiweekly, weekly, biweekly, every three weeks, every four weeks, monthly, bimonthly, semimonthly, every three months, every four months, semiannually, annually, or according to a combination of any of the above to arrive at a suitable dosing schedule. For example, a therapeutically relevant dose can be administered one or more times daily (up to 10 times daily for the highest dose) for one or more weeks.

Suitable doses of MG53 that can be administered to a subject in one or more dosage forms include at least 1 ng of MG53, at least 5 ng of MG53, at least 10 ng of MG53, at least 25 ng of MG53, at least 50 ng of MG53, at least 75 ng of MG53, at least 100 ng of MG53, at least 250 ng of MG53, at least 500 ng of MG53, at least 750 ng of MG53, at least 1 microg of MG53, at least 5 microg of MG53, at least 10 microg of MG53, at least 15 microg of MG53, at least 20 microg of MG53, at least 25 microg of MG53, at least 30 microg of MG53, at least 50 microg of MG53, or at least 100 microg of MG53. Such doses can be on a total body weight basis or a per kg of body weight basis.

The dose of exogenous MG53 can be as low as about 1 microg per kg of body weight up to about 1000 microg per kg of body weight.

The term "unit dosage form" is used herein to mean a dosage form containing a quantity of the MG53, said quantity being such that one or more predetermined units may be provided as a single therapeutic administration.

The dosage form is independently selected at each occurrence from the group consisting of liquid solution, suspension, tablet, pill, vial, powder, granule, bead, caplet, capsule, sachet or powder.

Compositions and dosage forms of the invention can further comprise one or more pharmaceutically acceptable excipients. Dosage forms can comprise one or more excipients independently selected at each occurrence from the group consisting of acidic agent, alkaline agent, buffer, tonicity modifier, osmotic agent, water soluble polymer, water-swellable polymer, thickening agent, complexing agent, chelating agent, penetration enhancer. Suitable excipients include U.S.F.D.A. inactive ingredients approved for use in parenteral or oral formulations (dosage forms), such as those listed in the U.S.F.D.A.'s "Inactive Ingredients Database (available on the following website: www.fda.gov/Drugs/InformationOnDrugs/ucm113978.htm; October 2018), the entire disclosure of which is hereby incorporated by reference.

As used herein, an acidic agent is a compound or combination of compounds that comprises an acidic moiety. Exemplary acidic agents include organic acid, inorganic acid, mineral acid and a combination thereof. Exemplary acids include hydrochloric acid, hydrobromic acid, sulfuric acid, sulfonic acid, sulfamic acid, phosphoric acid, or nitric acid or others known to those of ordinary skill; and the salts prepared from organic acids such as amino acids, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, others acids known to those of ordinary skill in the art, or combinations thereof.

As used herein, an alkaline agent is a compound or combination of compounds that comprises an alkaline moiety. Exemplary alkaline agents include primary amine, secondary amine, tertiary amine, quaternary amine, hydroxide, alkoxide, and a combination thereof. Exemplary alkaline agents include ammonia solution, ammonium carbonate, diethanolamine, monoethanolamine, potassium hydroxide, sodium borate, sodium carbonate, sodium bicarbonate, sodium hydroxide, triethanolamine, diethanolamine, monobasic phosphate salt, dibasic phosphate salt, organic amine base, alkaline amino acids and trolamine, others known to those of ordinary skill in the art, or combinations thereof.

Exemplary excipients (inactive ingredients as defined by the U.S.F.D.A.) that can be included in dosage forms of the invention include, by way of example and without limitation, water, benzalkonium chloride, glycerin, sodium hydroxide, hydrochloric acid, boric acid, hydroxyalkylphosphonate, sodium alginate, sodium borate, edetate disodium, propylene glycol, polysorbate 80, citrate, sodium chloride, polyvinylalcohol, povidone, copovidone, carboxymethylcellulose sodium, Dextrose, Dibasic Sodium Phosphate, Monobasic Sodium Phosphate, Potassium Chloride, Sodium Bicarbonate, Sodium Citrate, Calcium Chloride, Magnesium Chloride, stabilized oxychloro complex, Calcium Chloride Dihydrate, Erythritol, Levocarnitine, Magnesium Chloride Hexahydrate, Sodium Borate Decahydrate, Sodium Citrate Dihydrate, Sodium Lactate, Sodium Phosphate (Mono- and Dibasic-), Polyethylene Glycol 400, Hydroxypropyl Guar, Polyquaternium-1, Zinc Chloride, white petrolatum, mineral oil, hyaluronic acid, artificial tear, or combinations thereof.

One or more antioxidants can be included in a composition or dosage form of the invention. Exemplary antioxidants include SS-31, NAC, glutathione, selenium, vitamin A, vitamin C, vitamin E, co-enzyme Q10, resveratrol, other GRAS antioxidant, or a combination of two or more thereof.

One or more zinc salts can be included in a composition or dosage form of the invention. Such zinc salt(s) may also be administered to a subject receiving exogenous MG53 or expressed MG53. Pharmaceutically acceptable zinc salts include Zinc gluconate, Zinc acetate, Zinc sulfate, Zinc picolinate, Zinc orotate, Zinc citrate, and other such salts comprising a zinc cation and organic or inorganic anion(s).

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

As used herein, "pharmaceutically acceptable salts" refer to derivatives of the disclosed compounds wherein the compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts can be synthesized from the parent therapeutic compound which contains a basic or acidic moiety by conventional chemical methods. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The therapeutically acceptable dose, maximum tolerated dose (MTD), and minimally effective dose (MED) for each of said active ingredients is well known and set forth in the respective U.S.F.D.A. approved product package insert for each said active ingredients.

A composition, dosage form or formulation of the invention can include one, two or more active ingredients in combination with MG53. The dose of each said active ingredient in said composition, dosage form or formulation of the invention will be a therapeutically effective dose including and above the MED and including and below the MTD.

In some embodiments, the combination treatment of MG53 with another active ingredient provides at least additive therapeutic efficacy. In some embodiments, said combination provides synergistic therapeutic efficacy. In some embodiments, MG53 reduces the occurrence of, reduces the level of, or eliminates adverse events caused by the other active ingredient.

The acceptable concentrations of said excipients are well known in the art and specific concentrations (amounts) thereof are set forth in the package insert or package label of known commercial products containing the same.

It should be understood that compounds used in the art of pharmaceutics may serve a variety of functions or purposes. Thus, if a compound named herein is mentioned only once or is used to define more than one term herein, its purpose or function should not be construed as being limited solely to that named purpose(s) or function(s).

As used herein, the terms "about" or "approximately" are taken to mean a variation or standard deviation of ±10%, ±5%, or ±1% of a specified value. For example, about 20 mg is taken to mean 20 mg±10%, which is equivalent to 18-22 mg.

As used herein, the term "prodrug" is taken to mean a compound that, after administration, is converted within a subject's body, e.g. by metabolism, hydrolysis, or biodegradation, into a pharmacologically active drug. The prodrug may be pharmacologically active or inactive. For example, a prodrug of MG53 (native or mutant) would be converted to the native form or mutant form, respectively, of MG53. The term "precursor" may also be used instead of the term "prodrug".

As used herein, the term "derivative" is taken to mean: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

In the examples below, ranges are specified for the amount of each ingredient. Ranges including "0" as the lowest value indicate an optional ingredient. The lower limit ">0" indicates the respective material is present.

Compositions with quantities of ingredients falling within the compositional ranges specified herein were made. Compositions of the invention comprising quantities of ingredients falling within the compositional ranges specified herein operate as intended and as claimed.

In view of the above description and the examples below, one of ordinary skill in the art will be able to practice the invention as claimed without undue experimentation. The foregoing will be better understood with reference to the following examples that detail certain procedures for the preparation and use of compositions according to the present invention. All references made to these examples are for the purposes of illustration. The following examples should not be considered exhaustive, but merely illustrative of only a few of the many embodiments contemplated by the present invention. The methods described herein can be followed to prepare and use compositions of the invention and to practice methods of the invention.

MG53 was kindly provided by TRIM-edicine, Inc. (1275 Kinnear R D, Columbus Ohio 43212-1155, U.S.A.). We thank Dr. Wayne Chen for providing the doxycycline inducible RyR2 expressing HEK293 cells, Drs. Juan Moliva and Jordi Torrelles for providing the primary human blood monocyte-derived macrophage protein lysates, and Dr. Dominique Garcin for providing SeV-GFP.

EXAMPLE 1

In Vitro Assay in THP1 Cells: SeV

Sendai virus (SeV) expressing GFP, SeV strain Cantell, PR8 were propagated in embryonated chicken eggs and titered on LLCMK2 cells for SeV and MDCK cells for influenza virus. SeV-GFP and SeV infections were allowed to proceed for 24 or 48 hours using multiplicity of infections (MOIs) of 2 and 5 respectively. 24 hrs post SeV-GFP infection, THP1 cells were washed in PBS and fixed using 4% paraformaldehyde. Cells were washed, resuspended in PBS, and analyzed with a FACSCanto II flow cytometer (BD Biosciences) to determine the percentage of GFP positive cells. Data was analyzed using FlowJo software.

EXAMPLE 2

In Vitro Assay in THP1 Cells: SeV and H1N1 Influenza

Sendai virus (SeV) expressing GFP, SeV strain Cantell, and influenza virus strain PR8 were propagated in embryonated chicken eggs and titered on LLCMK2 cells for SeV and MDCK cells for influenza virus. SeV-GFP and SeV infections were allowed to proceed for 24 or 48 hours using multiplicity of infections (MOIs) of 2 and 5 respectively. 24 hrs post SeV-GFP infection, THP1 cells were washed in PBS and fixed using 4% paraformaldehyde. Cells were washed, resuspended in PBS, and analyzed with a FACSCanto II flow cytometer (BD Biosciences) to determine the percentage of GFP positive cells. Data was analyzed using FlowJo software.

EXAMPLE 3

Knockdown of MG53 in THP1 Cells

Control shRNA (SEQ ID 1: 5'-GACTGACATGT-CAAGCTGTAC-3') and MG53 shRNA (SEQ ID 2: 5'-GAAGAGTGTGGCTGTGCTGGAGCATCAGC-3') were ligated into pKLO-mcherry-puro vector. In brief, HEK293-FT cells were transfected with packaging, envelope, and target plasmids. Media was changed 18 hours after transfection, followed by collection of virus-containing media 48 hours later. Virus-containing media was centrifuged at 1200×g for 5 min and filtered with 0.45 μm filters. THP1 cells were then incubated with viral media. After 24 hrs, media was replaced, and cells were allowed 48 hrs to recover. Following recovery, cells were selected for using puromycin (1.0 μg/mL), and subsequently cultured in RPMI-1640 media supplemented with puromycin (0.5 μg/mL), to generate sh-control and sh-MG53 THP1 cells.

EXAMPLE 4

In Vivo Model: MG53 WT Vs KO Mice Treated with Influenza

MG53 knockout mice were generated in the 129S1/SvlmJ strain of mice. All mice were housed and handled following IACUC approved protocols. Murine intranasal influenza virus infections were carried out in 12-week-old male MG53 wild type and knockout mice. Animals were anesthetized using isoflurane and were intranasally infected with influenza virus strain A/PR/8/34 (H1N1) (PR8) at a dose of 10 tissue culture infectious dose 50 (TCID50) in 50 μL clinical grade saline. Mice were monitored daily and weights were recorded. Animals were euthanized at either day 5 post infection or at the experimental endpoint when they recovered to normal body weight. After animals were sacrificed, lungs and hearts were collected for viral titers, cytokine measurements, and histology.

EXAMPLE 5

Mortality in Wt Mice Infected with Influenza

Eight-week-old WT C57BL/6J mice (Jackson laboratories) were intranasally infected with 100 TCID50 Influenza A virus A/PR/8/34 (H1N1) in 50 ml sterile saline. Mice were monitored daily for body mass and survival. Mice reaching 30% body mass loss with hunched posture and lack of movement were considered moribund and removed from the study.

EXAMPLE 6

THP1 Cell Culture

THP1 cells were purchased from ATCC and cultured in RPMI-1640 media supplemented with L-Glutamine and sodium pyruvate (Sigma R8758) in addition to 10% fetal bovine serum and 1% penicillin/streptomycin in a 5% CO2 incubator. THP1 cells were differentiated using 100 ng/mL PMA (Sigma P1585) for 48 hrs. HEK293 and HEK293FT cells were obtained from ATCC and cultured using Dulbecco's modified Eagle's medium (DMEM) supplemented with 10% fetal bovine serum and 1% penicillin/streptomycin in a 5% CO2 incubator. HEK293-RyR2 cells were provided by Dr. Wayne Chen[47]. These cells possess doxycycline-inducible RyR2 expression, which enables spontaneous calcium oscillation in response to elevated extracellular calcium via store-overload induced calcium release. Cells were cultured using DMEM supplemented with 10% fetal bovine serum and 1% penicillin/streptomycin in a 5% CO2 incubator. Treatment with doxycycline (1 μg/mL) for 24 hrs was used to induce RyR expression.

EXAMPLE 7

Western Blot Analyses

Cells and murine skeletal muscle were lysed in radio-immunoprecipitation assay lysis buffer (Alfa Aesar, J63306) containing protease and phosphatase inhibitors. Cellular debris was pelleted via centrifugation and supernatants were collected for protein quantification by Bradford assay. Samples were prepared in 2× Laemlli sample buffer and separated on SDS-PAGE gels via electrophoresis, followed by wet transfer onto PVDF membrane. Membranes were blocked in 5% milk in TBS-T and probed with antibodies against MG53 (custom-made rabbit monoclonal antibody), glyceraldehyde 3-phosphate dehydrogenase (GAPDH; Cell Signaling Technology (CST) catalog #2118), p65 (CST 8242), phospho-p65 (CST 3033), or RyR (Invitrogen MA3925).

EXAMPLE 8

Oral Dosage Form of rhMG53 and EUDRAGIT S-100 rhMG53 is provided by TRIM-edicine, Inc. (Columbus, Ohio). EUDRAGIT S-100 (Poly(methacylic acid-co-methyl methacrylate) 1:2) is provided by EVONIK (healthcare.evonik.com/product/health-care/en/). The following procedure is used to prepare beads.

In a 100 mL beaker, add 35 mL water, and stir. While stirring add Eudragit S-100 powder (1.4 g), then and 12N NH$_4$OH (0.82 mL). Add 2-hydroxypropyl)-β-cyclodextrin (0.24 g) to a 10 mL water (CD: 24 mg/mL). Prepare a solution of MG53 (70 mg in ~15.5 mL PBS) at a pH 8. To this solution, add 10 mL of the CD solution and 10 mL of water for a total volume of 35.55 mL. Mix the MG53/CD solution with the Eudragit solution while stirring.

Spray dry the resulting suspension to form the powdered dosage form containing MG53 (70 mg), EUDRAGIT (1.4 g), salts (130 mg), and CD (0.24 g) for a total solids content of 1.77 g or a MG53-loading of 40 mg/g of solid (4% loading). Spray drying conditions used: nozzle size—0.6 mm; air speed—0.3 m³/min; air outlet temp: 38 C; room temperature: 24 C; room humidity: 53%.

The powder can be included in a capsule, caplet, tablet or other oral dosage form.

EXAMPLE 9

Preparation of MG53-Containing Enteric Release Composition

The enteric release formulation comprises MG53, hydroxypropyl-beta-cyclodextrin (HP-b-CD), and methacrylic acid/methyl methacrylate anionic copolymer (EUDRAGIT S 100; dissolution in water at pH above 7.0). The following procedure was used.
1. In a 100 mL beaker, added 35 mL water;
2. weighed 1.4 g Eudragit S-100 powder and added to the $H_2O$ above while stirring;
3. added 0.82 mL of 12N $NH_4OH$ and stirred continuously for half an hour while periodically checking pH;
4. weighed 0.24 g of 2-hydroxypropyl)-β-cyclodextrin and added to a vial containing 10 mL water (CD: 24 mg/mL);
5. added 70 mg MG53 to 15.5 mL PBS at pH 8;
6. mixed the HP-b-CD solution with the MG53-containing solution and add water to a total volume of 35.55 mL;
7. added the MG53/CD solution to the 35 mL Eudragit-containing solution while stirring, and added 1 mL of water;
6. spray dried the MG53/CD/EUDRAGIT solution according to Example 11;

The resulting enteric release composition contained: MG53 70 mg; Eudragit 1.4 g; salts: 15.5/2*17 mg/mL=130 mg; CD 0.24 g.

EXAMPLE 10

Determination of In-Vitro Release Profile

A known amount of powdered samples of MG53 containing enteric release composition (made according to Example 9) was dispersed in pH 2 (0.01N HCl) solution for 2 hrs, followed by addition of Na3PO4 solution (9.7 g in 112.8 mL $H_2O$; to pH 6.5), then followed by addition of same Na3PO4 solution to pH 7.5. At different time points, the released MG53 solution was centrifuged at 17,000 g for 20 min, filtered through 0.22 um filter, and the absorbance at 280 nm was measured (n=2 per time points). The release experiments were performed in an orbital shaker at 37° C. and 150 rpm.

EXAMPLE 11

Spraying Drying of MG53/CD/EUDRAGIT Mixture

The MG53/CD/EUDRAGIT mixture was produced by spray-drying using the laboratory scale ProCept 4M8-TriX spray-dryer (Zelzate, Belgium). Drug-polymer solutions were prepared in the binary solvent mixture of interest DCM/EtOH 2:1 (v/v) at 50 mg/mL. The feed solution flow rate was adjusted at 5 g/min. An atomizing air pressure of 0.65 bars was applied to a 1.2 mm bifluid nozzle to create a spray. The drying gas airflow was set at 0.35 m3/min and maintained at 65° C. The lateral cooling air was kept constant at 100 L/min and dried particles were separated from the exhaust air within the medium cyclone (height/diameter of 242 mm/60 mm). After processing, the spray-dried material was stored in a vacuum oven for 48 h before analysis to eliminate the last traces of residual solvent.

EXAMPLE 12

Co-Immunoprecipitation

Tissue and cells were lysed in radio-immunoprecipitation (IP) assay lysis buffer and assayed for protein concentration as stated above. 20 μL of magnetic protein G beads (per IP sample) were washed in PBS three times and conjugated to 2 μg (per IP sample) of antibody (MG53, RyR, Mouse and Rabbit IgG) for 2 hours at room temperature while rocking. Bead-antibody conjugates were then washed 2 times with PBS and once with lysis buffer. 1 mg of protein lysate was added to beads and then samples were incubated at 4° C. overnight while rocking. The following day, samples were washed 3 times in PBS and protein was eluted with 4% SDS and 2× Laemlli sample buffer. IP samples were then analyzed following the western blotting protocol stated earlier.

EXAMPLE 13

Masson's Trichrome Staining

The following procedure was used to determine the level of fibrosis in lung tissue.
1. Deparaffinize the paraffin embedded lung tissue block and rehydrate through 100% alcohol, 95% alcohol 70% alcohol. Wash in distilled water.
2. For Formalin fixed tissue, re-fix in Bouin's solution for 1 hour at 56 C to improve staining quality although this step is not absolutely necessary.
3. Rinse in running tap water for 5-10 minutes to remove the yellow color. Stain in Weigert's iron hematoxylin working solution for 10 minutes.
4. Rinse in running warm tap water for 10 minutes.
5. Wash in distilled water.
6. Stain in Biebrich scarlet-acid fuchsin solution for 10-15 minutes. Solution can be saved for future use.
7. Wash in distilled water.
8. Differentiate in phosphomolybdic-phosphotungstic acid solution for 10-15 minutes or until collagen is not red.
9. Transfer sections directly (without rinse) to aniline blue solution and stain for 5-10 minutes. Rinse briefly in distilled water and differentiate in 1% acetic acid solution for 2-5 minutes.
10. Wash in distilled water.
11. Dehydrate very quickly through 95% ethyl alcohol, absolute ethyl alcohol (these step will wipe off Biebrich scarlet-acid fuchsin staining) and clear in xylene.
12. Mount with resinous mounting medium.

EXAMPLE 14

Treatment of COVID-19 (SARS-COV-2) Infection in a Subject

Method A. MG53 Composition Therapy

A subject presenting with COVID-19 virus infection is prescribed MG53 composition, and therapeutically relevant doses are administered to the subject according to a prescribed dosing regimen for a period of time. The subject's level of therapeutic response (in terms of performance of one or more organs) is determined periodically. If the level of therapeutic response is too low at one dose, then the dose is escalated according to a predetermined dose escalation schedule until the desired level of therapeutic response in the subject is achieved. Treatment of the subject with MG53 is continued as needed and the dose or dosing regimen can be adjusted as needed until the patient reaches the desired clinical endpoint.

Method B. Combination Therapy: MG53 and Antiviral Agent

Method A, above, is followed except that the subject is prescribed and administered one or more other antiviral agents for the treatment of COVID-19 virus infection or symptoms thereof. Then one or more other antiviral agents can be administered before, after or with the MG53. Dose escalation (or de-escalation) of the one or more other antiviral agents can also be done.

EXAMPLE 15

Determination of Impact of MG53 Upon SARS-CoV-2 Viral N-Protein Expression

The A549 cell line stably expressing hACE2-GFP was used for the infection of SARS-CoV-2 (10 mol) in the presence or absence of 10 μg/ml rhMG53. Cells without SARS-CoV-2 infection (mock) and with saline treatment served as the negative control. After 24 hours of SARS-CoV-2 infection, cells were subjected to fixation with 4% paraformaldehyde and staining with the primary antibody against SARS-CoV-2 nuclear (N) protein and the secondary antibody (APC conjugated goat anti-rabbit IgG), followed by FACS analysis. The data are detailed in FIGS. 9 and 10.

EXAMPLE 16

Figure 14:
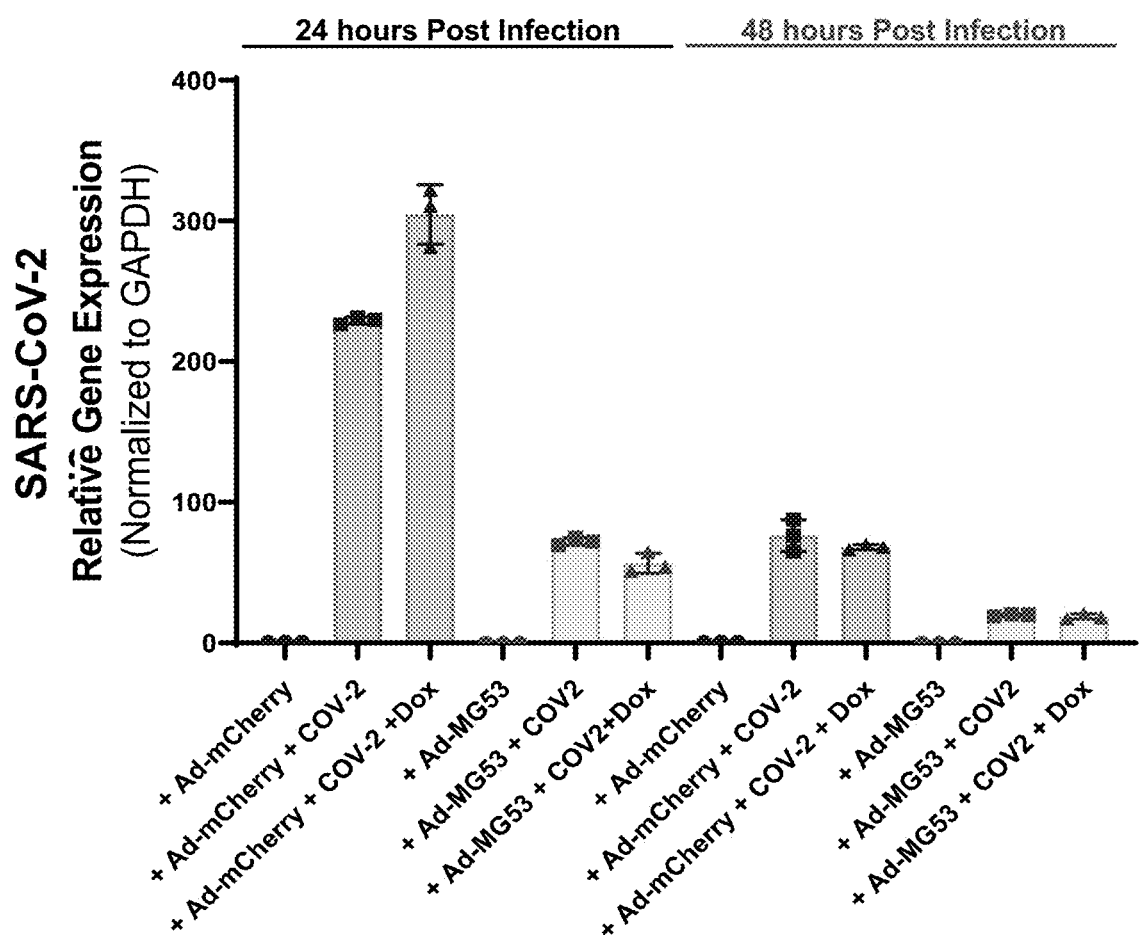
FIG. 14 depicts a chart of the relative expression of the SARS-CoV-2 N2 protein gene (normalized to GAPDH) for the BEAS-2B cells of FIG. 11.

Determination of Impact of MG53 Upon SARS-CoV-2 Viral Envelope and Nuclear Protein Gene Expression BEAS-2B cells, a cell line derived from normal bronchial epithelium obtained from autopsy of non-cancerous individuals, was infected with adenovirus (Ad) expressing MG53 (Ad-MG53) or vector as control (Ad-mCherry). BEAS-2B cells expressing MG53 or vector were then infected with SARS-CoV-2 (10 mol) and collected at 24 and 48 hours after SARS-CoV-2 infection. RT-qPCR were conducted for these samples with the primers specific for genes encoding MG53 (FIG. 11), SARS-CoV-2 envelope protein (FIG. 12), and nuclear proteins N1 (FIG. 13) and N2 (FIG. 14).

EXAMPLE 17

Determination of Impact of MG53 Upon SARS-CoV-2 Viral Envelope and Nuclear Protein Gene Expression Beating cardiomyocytes derived from human iPS cells (hiPSC-CMs) were subjected to SARS-CoV-2 infection (10 mol) and treatment with rhMG53 (0, 5, 120 microg/mL) at the same time. Non-infected hiPSC-CMs serve as mock control. The protocol is detailed in FIG. 15. Cells were collected for RNA extraction after 48 hours of SARS-CoV-2 infection. RT-qPCR were conducted for these samples with the primers specific for genes encoding SARS-CoV-2 envelop protein (E) and nuclear protein (N1 & N2). Data were normalized to GAPDH as internal control. Results are detailed in FIGS. 16-18.

All data are expressed as mean±S.D. Groups were compared by Student's t test and analysis of variance for repeated measures. A value of $p<0.05$ was considered significant.

For any range herein, the upper and lower limits thereof are considered as being part of the range. Moreover, all integer and fractional values within said ranges are also considered as being within said range. Accordingly, all integers and fractional values within each specified range are hereby incorporated by reference.

All values disclosed herein may have standard technical measure error (standard deviation) of ±10%. The term "about" or "approximately" is intended to mean±10%, ±5%, ±2.5% or ±1% relative to a specified value, i.e. "about" 20% means 20±2%, 20±1%, 20±0.5% or 20±0.25%. The term "majority" or "major portion" is intended to mean more than half, when used in the context of two portions, or more than one-third, when used in the context of three portions. The term "minority" or "minor portion" is intended to mean less than half, when used in the context of two portions, or less than one-third, when used in the context of three portions. It should be noted that, unless otherwise specified, values herein concerning pharmacokinetic or dissolution parameters are typically representative of the mean or median values obtained.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating COVID-19 comprising administering to a subject having or at risk of having a SARS-CoV-2 infection one or more therapeutically effective doses of native recombinant human MG53.

2. The method of claim 1, wherein said administering results in a) prevention of viral infection-induced organ failure; b) reversal of viral infection-induced organ failure; c) mitigating virus-infection induced organ fibrosis, which may or may not be fatal; or d) a combination of any thereof.

3. The method of claim 2, wherein a) said organ failure is short-term or acute organ failure, meaning organ failure that occurs over a period of hours, days, weeks or up to about three months; orb) said organ failure is long-term or chronic organ failure, meaning organ failure that occurs over a period of about three months or more.

4. The method of claim 2, wherein said organ is selected from the group consisting of the respiratory system, heart, lung, kidney, liver, gastrointestinal system.

5. The method of claim 1, wherein said MG53 is administered a) acutely, chronically, or a combination thereof; b) in one or more dosage forms exhibiting one or more release profiles selected from the group consisting of immediate release, rapid release, extended release, sustained release, controlled release, enteric release, and a combination of any thereof; c) orally, by injection, intravenously, intraarterially, subcutaneously, intramuscularly, rectally, by infusion, directly to a target organ, and/or transdermally; or d) a combination of any thereof.

6. The method of claim 1 further comprising the step of administering one or more therapeutically relevant doses of one or more antiviral agents to said subject.

7. The method of claim 6, wherein administration of MG53 and said one or more antiviral agents is separate, overlapping, sequential, or simultaneous.

8. A method of treating COVID-19 comprising administering to a subject having or at risk of having a SARS-CoV-2 infection plural therapeutically effective doses of native recombinant human MG53 over a period of at least 3 days, at least 5 days, at least one week, at least 10 days, or at least 2 weeks.

9. The method of claim 2, wherein said mitigating is ameliorating, treating, or curing said virus-infection induced organ fibrosis, which may or may not be fatal.

* * * * *